(12) United States Patent
Wickens et al.

(10) Patent No.: US 10,301,605 B2
(45) Date of Patent: May 28, 2019

(54) POLY(UG) POLYMERASE, CONSTRUCTS, AND METHODS OF MAKING AND USING THE SAME

(71) Applicant: Wisconsin Alumni Research Foundation, Madison, WI (US)

(72) Inventors: Marvin P. Wickens, Madison, WI (US); Melanie A. Preston, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 600 days.

(21) Appl. No.: 14/943,229

(22) Filed: Nov. 17, 2015

(65) Prior Publication Data

US 2016/0145666 A1 May 26, 2016

Related U.S. Application Data

(60) Provisional application No. 62/084,739, filed on Nov. 26, 2014.

(51) Int. Cl.
C12N 9/12 (2006.01)
C12P 19/34 (2006.01)
C12Q 1/6844 (2018.01)

(52) U.S. Cl.
CPC ............ *C12N 9/1247* (2013.01); *C12P 19/34* (2013.01); *C12Y 207/07* (2013.01); *C12Y 207/07006* (2013.01); *C12Q 1/6846* (2013.01)

(58) Field of Classification Search
CPC .......... C12Y 207/07; C12Y 207/07006; C12N 9/1247; C12P 19/34
See application file for complete search history.

(56) References Cited

PUBLICATIONS

Aphasizhev, et. al., Trypanosome mitochondrial 3' terminal uridylyl transferase (TUTase): The key enzyme in U-insertion/deletion RNA editing, Cell, 2002, 108, 637-648.
Coller, et al., Tethered function assays: An adaptable approach to study RNA regulatory proteins, Methods in Enzymology, 2007, 429, 299-321.
Kohlstaedt, et al., Reverse transcriptase of human immunodeficiency virus can use either human tRNA3Lys or *Escherichia coli* tRNA2Gln as a primer in an in vitro primer-utilization assay, PNAS, 1992, 89, 9652-9656.
Kwak, et al., A family of poly(U) polymerases, RNA, 2007, 13, 860-867.
Lingner, et al., 3'-end labeling of RNA with recombinant yeast poly(A) polymerase, Nucleic Acids Res, 1993, 21(12), 2917-2920.
Martin, et al., Tailing and 3'-end labeling of RNA with yeast poly(A) polymerase and various nucleotides, RNA, 1998 4, 226-230.
Moritz, et al., Simple methods for the 3' biotinylation of RNA, RNA, 2014, 20, 421-427.

(Continued)

*Primary Examiner* — Jeremy C Flinders
(74) *Attorney, Agent, or Firm* — Quarles & Brady LLP

(57) ABSTRACT

Methods, kits, and compositions of matter relating to poly (UG) polymerases are disclosed. In one embodiment, a method includes: contacting an RNA substrate with a poly (UG) polymerase; and allowing the poly(UG) polymerase to add a poly(UG) sequence to the end of the RNA substrate by retaining contact between the RNA substrate and the poly (UG) polymerase for a period of time from about 1 second to about 28 days. The poly(UG) polymerase can be *Caenorhabditis elegans* RDE-3.

12 Claims, 15 Drawing Sheets
(14 of 15 Drawing Sheet(s) Filed in Color)
Specification includes a Sequence Listing.

(56) References Cited

PUBLICATIONS

Myers, et al., RNA primer used in synthesis of anticomplementary DNA by reverse transcriptase of avian myeloblastosis virus, PNAS, 1980, 77(3), 1316-1320.
Read, et al., Cytoplasmic poly(A) polymerases mediate cellular responses to S phase arrest, PNAS, 2002, 99(19), 12079-12084.
Rissland, et al., Efficient RNA polyuridylation by noncanonical poly(A) polymerase, Mol Cell Biol, 2007, 27(10), 3612-3624.
Wahle, E., Purification and characterization of a mammalian polyadenylate polymerase involved in the 3' end processing of messenger RNA precursors, J Biol Chem, 1991, 266(5), 3131-3139.
Winz, et al., Site-specific terminal and internal labeling of RNA by poly(A) polymerase tailing and copper-catalyzed or copper-free strain-promoted click chemistry, Nucleic Acid Res., 2012, 40(10), e78.

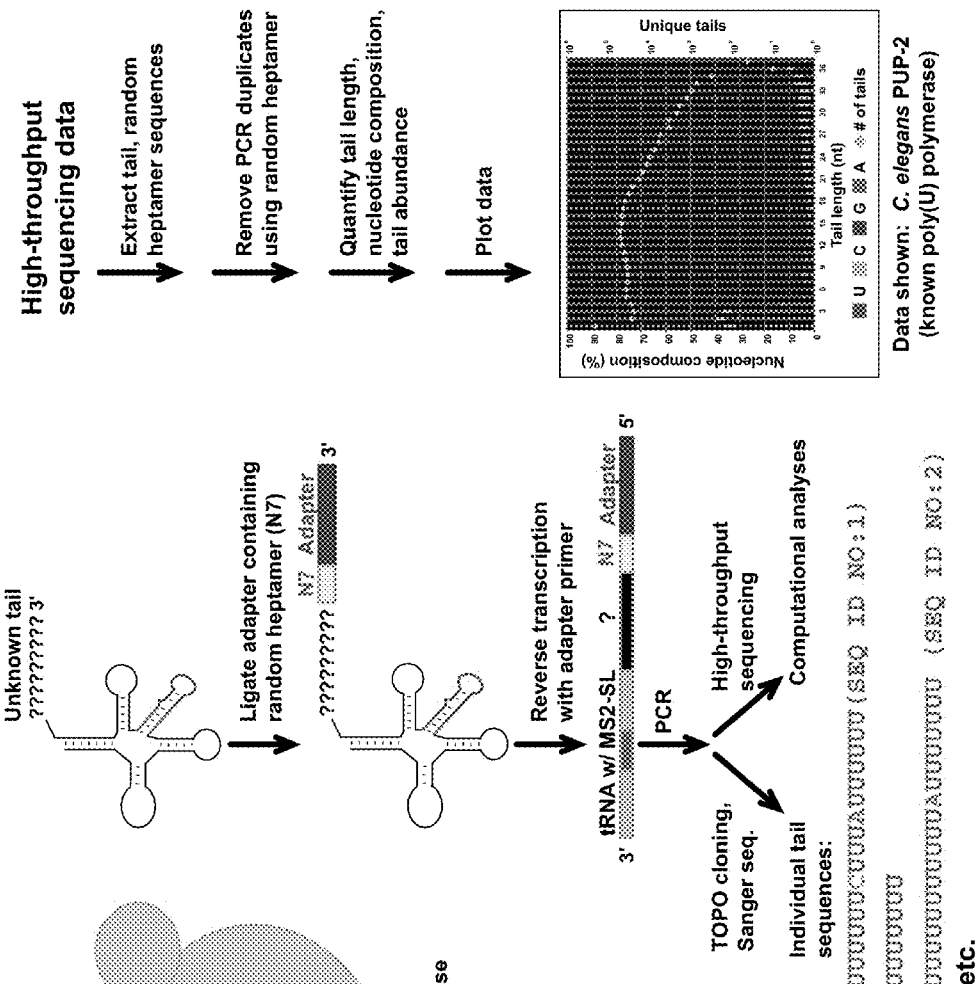
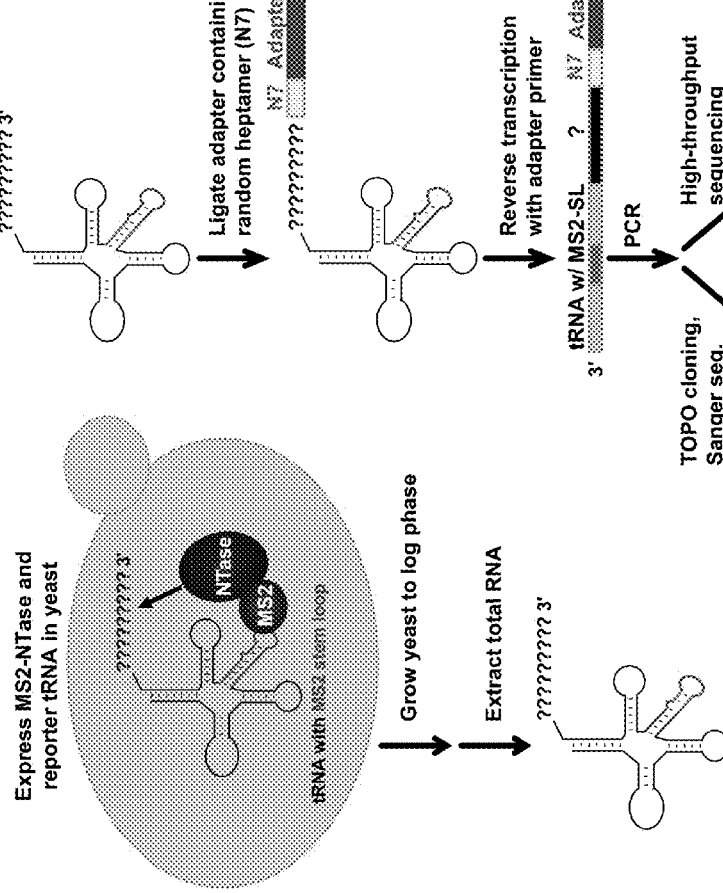
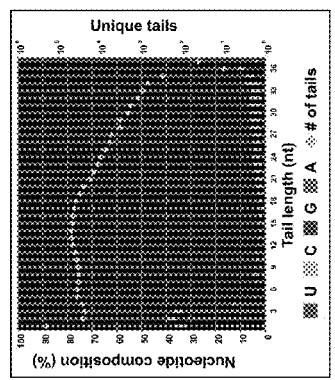
Figure 1A
Figure 1B
Figure 1C

Figure 2

Enzymes analyzed by the NTase assay

PUPs

Known:
- PUP-1
- PUP-2
- PUP-3
- Star-PAP
- TUT4
- TUT7
- Cid1

New:
- F43E2.1
- NCU04364

PAPs

Known:
- GLD-2
- GLD-4
- GLD2
- MTPAP
- PAPD5
- Star-PAP
- Cid13
- Cid14

New:
- F43H9.3
- C53A5.16
- ZK863.4
- PAPD7
- Cid11
- Cid12
- SPCC645.10
- TRF4
- CR_03940W
- NCU00538
- NCU11050
- TRF4
- cutA
- cutB

Unique activities
- F31C3.2
- RDE-3
- SPAC1093.04

Organisms: C. elegans, H. sapiens, S. pombe, C. albicans, N. crassa, A. nidulans

Figure 4

RDE-3 replicate #1

| RNA 3' end | Untemplated nucleotides added | # times observed |
|---|---|---|
| CCA | none | 13356 |
| CCA | GUGUG | 151 |
| CCA | UGUGU | 165 |
| CCA | GUGUGA | 28 |
| CCA | GUGUGU | 151 |
| CCA | UGUGUG | 214 |
| CCA | GUGUGUG | 121 |
| CCA | UGUGUGU | 126 |
| CCA | UGUGUGUG | 180 |
| CCA | UGUGUGUGU | 84 |
| CCA | GUGUGUGUGU | 26 |
| CCA | UGUGUGUGUG (SEQ ID NO:3) | 84 |
| CCA | UGUGUGUGUGUG (SEQ ID NO:4) | 41 |
| CCA | UGUGUGUGUGUG (SEQ ID NO:5) | |

RDE-3 replicate #2

| RNA 3' end | Untemplated nucleotides added | # times observed |
|---|---|---|
| CCA | none | 12455 |
| CCA | GUGUG | 565 |
| CCA | UGUGU | 331 |
| CCA | GUGUGA | 101 |
| CCA | GUGUGG | 33 |
| CCA | GUGUGU | 588 |
| CCA | UGUGUG | 302 |
| CCA | GUGUGUG | 370 |
| CCA | UGUGUGU | 255 |
| CCA | GUGUGUGU | 199 |
| CCA | UGUGUGUG | 245 |
| CCA | GUGUGUGUG | 143 |
| CCA | UGUGUGUGU | 127 |
| CCA | UGUGUGUGUG | 269 |
| CCA | UGUGUGUGUGU (SEQ ID NO:6) | |
| | UGUGUGUGUGUG (SEQ ID NO:7) | 95 |

Approximately 10% of sequenced tails contain UG repeats

Figure 11

| Mutation | Type | Biological Replicates | Activity |
|---|---|---|---|
| D105A/D107A | 2 catalytic Asp mutated to Ala | 3 | inactive |
| G93E | Gly of conserved GS motif | 2 | inactive |
| Δ113-221 | Deletes a portion of NTD | 3 | inactive |
| Δ164-end | Deletes a portion of NTD | 2 | inactive |
| Δ169-end | Deletes a portion of NTD | 2 | inactive |
| D189N | 3rd catalytic Asp | 2 | inactive |
| G366R | NRM | 4 | inactive/low |

Figure 15

RDE-3 is also known as MUT-2 and K04F10.6.
There are two transcriptional isoforms of RDE-3: K04F10.6a and K04F10.6b.
K04F10.6a has UG-adding activity, and K04F10.6b is inactive in the heterologous NTase assay.

DNA sequence of RDE-3 isoform a: (SEQ ID NO:52)
NCBI Reference Sequence: NM_059433.7
WormBase ID#: WBGene00003499

ATGTCTCAACAATAAAGATCAGCGAAGTCCAGAAGACATAGACTTTAAGGTCAAAGCGAATCCAAAAGCGTTTCACAAATTTAACGAAAGTTTCAACGCGTT
TTAAGGATCACGAGGAGACGGATTTCAATATATTGTCTCATCAGGATCATTTCGATACTCCAAAAGAGGAGTTCGGTAAAAAATGGATTGG
TGCTATCAGCTGAAGAATATAATTTCGAAGAACAATCCAACGTGCTATTCAATATCGTGCCAACTGGAAGTAACCGGATTGGCCACTAAAAACAGTGAT
CTAGACGTTGCAATTCATATCCACAAGCGGCAAGAGTTCGAACAAGAAGAAACGTGGAAGAAATATCACAGATGACGAACGATCATGGAGAGAAATT
CAATTGGAAATCCTACAAATTGTCCGTCTTAACTTACAAAATGATGAACAGATCAATTCAAGATCAGTTATGATCAGTGGAACATGGAAATCCAGCTCGTTCAAGCTCAAATT
CAAATTTGAAAGTGATGACGGTAGACGGAATCGATTGTGTATATCAGTCGAGTTAGTGATCGATTTCTGTCATCGATCCAAAAGATCCAAAAGATGAGGATTCAACAGTTATGCA
GCACATATCGACGGCCGATTTGCACCATTATGGTCGAATCGTAAAACATGGCAGCCAGTACATTTCCACAATACTGCCAAATTTGCCCCAAGAATTCTTAAAAGGATAATTCATTGCTTGGGATGAC
CTTGTTCTACTGGTGATTCACTTCCTCCAATGCGTGCACCACTTCAAGATTTGGTGCACCACTACATTGGTGCCAGGCCTGTAAGTGCCCTGAAGAACTGTAAGAACATTGATCATGGAACATTGAATGAACAATTAAAGATGTTATGAAGAAGCACATATCAGAAG
AAAGTCTATCATCAATTTGAATTTTGGTGCACCACTTCAAAGAAAACTACATTGGTGCCAGGCCTGTAAGAACTGTAAGAACATTGATCATGGAACATTGAATGAACAATTAAAGATGTTATGAAGAAGCACATATCAGAAG
TATTACTACTCGATGTGTATTCAAGATCCATTCGAATTCACGTTTCTACAATCGTTTCTACAAGTGCTAACTGTAAGTGCTCCAGAAGTGCCTAAACCATCGCGTGCAGAAGTTCGAAACTTC
TTTCTCCCTGTCGAAGGCTCCGAATTCACGTTTCTACAATCGTTTCTACAATGTCTACCAGAAGTGCCTAAACCATCGCGTGCAGAAGTTCGAAACTTC
CGAGCTGAAGCCACAGAAGCCAGAAGTGAATCGAGTCGGCTTAGGTGTCTACTGCCGAACTCATTTGTATAG

Protein sequence of RDE-3 isoform a: (SEQ ID NO:53)
NCBI Reference Sequence: NP_491834.1
WormBase ID: WP:CE11740

MSQPNKDQRSPEDIDFKVKANPKAFHKFNGKFQRVLRDHEDDFNILSIMQDHFDTTKQPKEFGKKMDWCYQLKNIISKNNPTWLFNIVPTGSTVTGLATKNSD
LDVAIHIPQAARVLEQEERGRNITDDERQASWREIQLEILQIVRLNLQNDEQINSRINWERGIQLVQAQIQILKVMTVDGIDCDISVMDRFLSSMHNSFLIRHL
AHIDGRFAPLCAIVKQWAASTKVKDPKDGGFNSYALVLLVIHFLQCGTFPPILPNLQEIFKKDNPIAWDDKVYPSILNFGAPLPKPLRIAPNNAPLARLFIEFL
YYYSMFNFKENYIGARPVMVMDRRTSQNNMVRSSTNKEVCIQDPFDEHNPGRTVRTLMRIKDVMRSTYQKFLPVEGSEFTFPTLEDIINMSPEVPKPSRAEVRNF
RAEATEVNRVGLGVYCRNSFV

SEQUENCE LISTING

<160> NUMBER OF SEQ ID NOS: 54

<210> SEQ ID NO 1
<211> LENGTH: 17
<212> TYPE: RNA
<213> ORGANISM: Artificial Sequence
<220> FEATURE:
<223> OTHER INFORMATION: synthetic sequence

<400> SEQUENCE: 1
uuuuuucuuu auuuuuu                                                   17

<210> SEQ ID NO 2
<211> LENGTH: 19
<212> TYPE: RNA
<213> ORGANISM: Artificial Sequence
<220> FEATURE:
<223> OTHER INFORMATION: synthetic sequence

<400> SEQUENCE: 2
uuuuuuuuuu uauuuuuuu                                                 19

<210> SEQ ID NO 3
<211> LENGTH: 10
<212> TYPE: RNA
<213> ORGANISM: Artificial Sequence
<220> FEATURE:
<223> OTHER INFORMATION: synthetic sequence

<400> SEQUENCE: 3
gugugugugu                                                           10

<210> SEQ ID NO 4
<211> LENGTH: 10
<212> TYPE: RNA
<213> ORGANISM: Artificial Sequence
<220> FEATURE:
<223> OTHER INFORMATION: synthetic sequence

<400> SEQUENCE: 4
ugugugugug                                                           10

<210> SEQ ID NO 5
<211> LENGTH: 12
<212> TYPE: RNA
<213> ORGANISM: Artificial Sequence
<220> FEATURE:
<223> OTHER INFORMATION: synthetic sequence

<400> SEQUENCE: 5
ugugugugug ug                                                        12

<210> SEQ ID NO 6
<211> LENGTH: 10
<212> TYPE: RNA
<213> ORGANISM: Artificial Sequence
<220> FEATURE:
<223> OTHER INFORMATION: synthetic sequence

<400> SEQUENCE: 6
ugugugugug                                                           10

<210> SEQ ID NO 7
<211> LENGTH: 12
<212> TYPE: RNA
<213> ORGANISM: Artificial Sequence

```
<220> FEATURE:
<223> OTHER INFORMATION: synthetic sequence

<400> SEQUENCE: 7
ugugugugug ug                                                               12

<210> SEQ ID NO 8
<211> LENGTH: 10
<212> TYPE: RNA
<213> ORGANISM: Artificial Sequence
<220> FEATURE:
<223> OTHER INFORMATION: synthetic sequence

<400> SEQUENCE: 8
gugugugugu                                                                  10

<210> SEQ ID NO 9
<211> LENGTH: 11
<212> TYPE: RNA
<213> ORGANISM: Artificial Sequence
<220> FEATURE:
<223> OTHER INFORMATION: synthetic sequence

<400> SEQUENCE: 9
gugugugugu g                                                                11

<210> SEQ ID NO 10
<211> LENGTH: 12
<212> TYPE: RNA
<213> ORGANISM: Artificial Sequence
<220> FEATURE:
<223> OTHER INFORMATION: synthetic sequence

<400> SEQUENCE: 10
gugugugugu gu                                                               12

<210> SEQ ID NO 11
<211> LENGTH: 13
<212> TYPE: RNA
<213> ORGANISM: Artificial Sequence
<220> FEATURE:
<223> OTHER INFORMATION: synthetic sequence

<400> SEQUENCE: 11
gugugugugu gug                                                              13

<210> SEQ ID NO 12
<211> LENGTH: 11
<212> TYPE: RNA
<213> ORGANISM: Artificial Sequence
<220> FEATURE:
<223> OTHER INFORMATION: synthetic sequence

<400> SEQUENCE: 12
gugugugugu g                                                                11

<210> SEQ ID NO 13
<211> LENGTH: 12
<212> TYPE: RNA
<213> ORGANISM: Artificial Sequence
<220> FEATURE:
<223> OTHER INFORMATION: synthetic sequence

<400> SEQUENCE: 13
gugugugugu gu                                                               12
```

```
<210> SEQ ID NO 14
<211> LENGTH: 10
<212> TYPE: RNA
<213> ORGANISM: Artificial Sequence
<220> FEATURE:
<223> OTHER INFORMATION: synthetic sequence

<400> SEQUENCE: 14
gugugugugu                                                               10

<210> SEQ ID NO 15
<211> LENGTH: 11
<212> TYPE: RNA
<213> ORGANISM: Artificial Sequence
<220> FEATURE:
<223> OTHER INFORMATION: synthetic sequence

<400> SEQUENCE: 15
gugugugugu g                                                             11

<210> SEQ ID NO 16
<211> LENGTH: 12
<212> TYPE: RNA
<213> ORGANISM: Artificial Sequence
<220> FEATURE:
<223> OTHER INFORMATION: synthetic sequence

<400> SEQUENCE: 16
gugugugugu gu                                                            12

<210> SEQ ID NO 17
<211> LENGTH: 16
<212> TYPE: RNA
<213> ORGANISM: Artificial Sequence
<220> FEATURE:
<223> OTHER INFORMATION: synthetic sequence

<400> SEQUENCE: 17
guugugugug uuguuu                                                        16

<210> SEQ ID NO 18
<211> LENGTH: 33
<212> TYPE: RNA
<213> ORGANISM: Artificial Sequence
<220> FEATURE:
<223> OTHER INFORMATION: synthetic sequence

<400> SEQUENCE: 18
ugugugugug uugugugugu gugugugugu gug                                     33

<210> SEQ ID NO 19
<211> LENGTH: 23
<212> TYPE: RNA
<213> ORGANISM: Artificial Sequence
<220> FEATURE:
<223> OTHER INFORMATION: synthetic sequence

<400> SEQUENCE: 19
ugugugugug uguguguaau uag                                                23

<210> SEQ ID NO 20
<211> LENGTH: 16
<212> TYPE: RNA
<213> ORGANISM: Artificial Sequence
<220> FEATURE:
<223> OTHER INFORMATION: synthetic sequence
```

```
<400> SEQUENCE: 20
augugugugu gugugu                                                    16

<210> SEQ ID NO 21
<211> LENGTH: 14
<212> TYPE: RNA
<213> ORGANISM: Artificial Sequence
<220> FEATURE:
<223> OTHER INFORMATION: synthetic sequence

<400> SEQUENCE: 21
ugugugaguu ugug                                                      14

<210> SEQ ID NO 22
<211> LENGTH: 24
<212> TYPE: RNA
<213> ORGANISM: Artificial Sequence
<220> FEATURE:
<223> OTHER INFORMATION: synthetic sequence

<400> SEQUENCE: 22
uguguguuua ucuguguaug ugug                                           24

<210> SEQ ID NO 23
<211> LENGTH: 15
<212> TYPE: RNA
<213> ORGANISM: Artificial Sequence
<220> FEATURE:
<223> OTHER INFORMATION: synthetic seqeunce

<400> SEQUENCE: 23
ugugugaguu uuugu                                                     15

<210> SEQ ID NO 24
<211> LENGTH: 29
<212> TYPE: RNA
<213> ORGANISM: Artificial Sequence
<220> FEATURE:
<223> OTHER INFORMATION: synthetic sequence

<400> SEQUENCE: 24
ugugugugug ugugugugug ugugugugu                                      29

<210> SEQ ID NO 25
<211> LENGTH: 16
<212> TYPE: RNA
<213> ORGANISM: Artificial Sequence
<220> FEATURE:
<223> OTHER INFORMATION: synthetic sequence

<400> SEQUENCE: 25
ugugugugug ugugug                                                    16

<210> SEQ ID NO 26
<211> LENGTH: 19
<212> TYPE: RNA
<213> ORGANISM: Artificial Sequence
<220> FEATURE:
<223> OTHER INFORMATION: synthetic sequence

<400> SEQUENCE: 26
guguguguuu uugugaugu                                                 19

<210> SEQ ID NO 27
```

```
<211> LENGTH: 19
<212> TYPE: RNA
<213> ORGANISM: Artificial Sequence
<220> FEATURE:
<223> OTHER INFORMATION: synthetic sequence

<400> SEQUENCE: 27
uguguuuugu gugugugug                                                      19

<210> SEQ ID NO 28
<211> LENGTH: 19
<212> TYPE: RNA
<213> ORGANISM: Artificial Sequence
<220> FEATURE:
<223> OTHER INFORMATION: synthetic sequence

<400> SEQUENCE: 28
gugugauuuu uugugugug                                                      19

<210> SEQ ID NO 29
<211> LENGTH: 16
<212> TYPE: RNA
<213> ORGANISM: Artificial Sequence
<220> FEATURE:
<223> OTHER INFORMATION: synthetic sequence

<400> SEQUENCE: 29
gugugugugu guguuu                                                         16

<210> SEQ ID NO 30
<211> LENGTH: 11
<212> TYPE: RNA
<213> ORGANISM: Artificial Sequence
<220> FEATURE:
<223> OTHER INFORMATION: synthetic sequence

<400> SEQUENCE: 30
uguuuuuuuu u                                                              11

<210> SEQ ID NO 31
<211> LENGTH: 16
<212> TYPE: RNA
<213> ORGANISM: Artificial Sequence
<220> FEATURE:
<223> OTHER INFORMATION: synthetic sequence

<400> SEQUENCE: 31
ugugugugug ugugug                                                         16

<210> SEQ ID NO 32
<211> LENGTH: 23
<212> TYPE: RNA
<213> ORGANISM: Artificial Sequence
<220> FEATURE:
<223> OTHER INFORMATION: synthetic sequence

<400> SEQUENCE: 32
ugugugugug ugugugugug ugu                                                 23

<210> SEQ ID NO 33
<211> LENGTH: 14
<212> TYPE: RNA
<213> ORGANISM: Artificial Sequence
<220> FEATURE:
<223> OTHER INFORMATION: synthetic sequence

<400> SEQUENCE: 33
```

```
uguguugugu gugu                                                14

<210> SEQ ID NO 34
<211> LENGTH: 10
<212> TYPE: RNA
<213> ORGANISM: Artificial Sequence
<220> FEATURE:
<223> OTHER INFORMATION: synthetic sequence

<400> SEQUENCE: 34
gauuuuguuu                                                     10

<210> SEQ ID NO 35
<211> LENGTH: 29
<212> TYPE: RNA
<213> ORGANISM: Artificial Sequence
<220> FEATURE:
<223> OTHER INFORMATION: synthetic sequence

<400> SEQUENCE: 35
ugugugugug ugugugugug ugugugugu                                29

<210> SEQ ID NO 36
<211> LENGTH: 15
<212> TYPE: RNA
<213> ORGANISM: Artificial Sequence
<220> FEATURE:
<223> OTHER INFORMATION: synthetic sequence

<400> SEQUENCE: 36
ugugugugug ugugu                                               15

<210> SEQ ID NO 37
<211> LENGTH: 16
<212> TYPE: PRT
<213> ORGANISM: Artificial Sequence
<220> FEATURE:
<223> OTHER INFORMATION: synthetic sequence

<400> SEQUENCE: 37

Gly Ser Thr Val Thr Gly Leu Ala Thr Lys Asn Ser Asp Leu Asp Val
1               5                   10                  15

<210> SEQ ID NO 38
<211> LENGTH: 21
<212> TYPE: DNA
<213> ORGANISM: Artificial Sequence
<220> FEATURE:
<223> OTHER INFORMATION: synthetic sequence

<400> SEQUENCE: 38
tggaattctc gggtgccaag g                                        21

<210> SEQ ID NO 39
<211> LENGTH: 22
<212> TYPE: DNA
<213> ORGANISM: Artificial Sequence
<220> FEATURE:
<223> OTHER INFORMATION: synthetic sequence

<400> SEQUENCE: 39
gccttggcac ccgagaattc ca                                       22

<210> SEQ ID NO 40
<211> LENGTH: 20
```

<212> TYPE: DNA
<213> ORGANISM: Artificial Sequence
<220> FEATURE:
<223> OTHER INFORMATION: synthetic sequence

<400> SEQUENCE: 40
gaggatcacc catgtcgcag                                              20

<210> SEQ ID NO 41
<211> LENGTH: 16
<212> TYPE: RNA
<213> ORGANISM: Artificial Sequence
<220> FEATURE:
<223> OTHER INFORMATION: synthetic sequence

<400> SEQUENCE: 41
ugugugugug ugugug                                                  16

<210> SEQ ID NO 42
<211> LENGTH: 16
<212> TYPE: RNA
<213> ORGANISM: Artificial Sequence
<220> FEATURE:
<223> OTHER INFORMATION: synthetic sequence

<400> SEQUENCE: 42
gugugugugu gugugu                                                  16

<210> SEQ ID NO 43
<211> LENGTH: 75
<212> TYPE: DNA
<213> ORGANISM: Artificial Sequence
<220> FEATURE:
<223> OTHER INFORMATION: synthetic sequence

<400> SEQUENCE: 43
aatgatacgg cgaccaccga gatctacacg ttcagagttc tacagtccga cgatcgagga    60
tcacccatgt cgcag                                                   75

<210> SEQ ID NO 44
<211> LENGTH: 25
<212> TYPE: DNA
<213> ORGANISM: Artificial Sequence
<220> FEATURE:
<223> OTHER INFORMATION: synthetic seqeunce

<400> SEQUENCE: 44
caaagcagaa gacggcatac gagat                                        25

<210> SEQ ID NO 45
<211> LENGTH: 33
<212> TYPE: DNA
<213> ORGANISM: Artificial Sequence
<220> FEATURE:
<223> OTHER INFORMATION: synthetic sequence

<400> SEQUENCE: 45
gtgactggag ttccttggca cccgagaatt cca                               33

<210> SEQ ID NO 46
<211> LENGTH: 44
<212> TYPE: DNA
<213> ORGANISM: Artificial Sequence
<220> FEATURE:
<223> OTHER INFORMATION: synthetic sequence

```
<400> SEQUENCE: 46
gaggatcacc catgtcgcag gttcgagtcc tgcagttgtc gcca            44

<210> SEQ ID NO 47
<211> LENGTH: 22
<212> TYPE: DNA
<213> ORGANISM: Artificial Sequence
<220> FEATURE:
<223> OTHER INFORMATION: synthetic sequence

<400> SEQUENCE: 47
gtctgcaggt cgactctaga aa                                    22

<210> SEQ ID NO 48
<211> LENGTH: 27
<212> TYPE: DNA
<213> ORGANISM: Artificial Sequence
<220> FEATURE:
<223> OTHER INFORMATION: synthetic sequence

<400> SEQUENCE: 48
ctctgcagtc gataaagaaa acatgag                               27

<210> SEQ ID NO 49
<211> LENGTH: 16
<212> TYPE: DNA
<213> ORGANISM: Artificial Sequence
<220> FEATURE:
<223> OTHER INFORMATION: synthetic sequence

<400> SEQUENCE: 49
cacacacaca cacaca                                           16

<210> SEQ ID NO 50
<211> LENGTH: 24
<212> TYPE: DNA
<213> ORGANISM: Artificial Sequence
<220> FEATURE:
<223> OTHER INFORMATION: synthetic sequence

<400> SEQUENCE: 50
ggcaacttgg ccgagtggtt aagg                                  24

<210> SEQ ID NO 51
<211> LENGTH: 29
<212> TYPE: DNA
<213> ORGANISM: Artificial Sequence
<220> FEATURE:
<223> OTHER INFORMATION: synthetic sequence

<400> SEQUENCE: 51
cacacacaca cacacatggc gacaactgc                             29

<210> SEQ ID NO 52
<211> LENGTH: 1326
<212> TYPE: DNA
<213> ORGANISM: Caenorhabditis elegans

<400> SEQUENCE: 52
atgtctcaac caaataaaga tcagcgaagt ccagaagaca tagactttaa ggtcaaagcg    60
aatccaaaag cgtttcacaa atttaacgga aagtttcaac gcgttttaag ggatcacgag   120
gacgatttca atatattgtc tatcagtatg caggatcatt tcgatactac gaaacagcca   180
aaagaggagt tcggtaaaaa aatggattgg tgctatcagc tgaagaatat aatttcgaag   240
```

```
aacaatccaa cgtggctatt caatatcgtg ccaactggaa gtacagtaac cggattggcc    300
actaaaaaca gtgatctaga cgttgcaatt catatcccac aagcggcaag agttctggaa    360
caagaagaac gtggaagaaa tatcacagat gacgaacgac aagcatcatg gagagaaatt    420
caattggaaa tcctacaaat tgtccgtctt aacttacaaa atgatgaaca gatcaattca    480
agaattaatt gggaacatgg aatccagctc gttcaagctc aaattcaaat tttgaaagtg    540
atgacggtag acggaatcga ttgtgatatc agtgtagtta tggatcgatt tctgtcatcg    600
atgcacaatt cttttttgat tcgacatttg gcacatatcg acggccgatt tgcaccatta    660
tgtgcaatcg taaacaatg ggcagccagt acaaaagtta aagatccaaa agatggagga    720
ttcaacagtt atgcacttgt tctactggtg attcacttcc tccaatgcgg tacatttcca    780
ccaatactgc caaatttgca agaaatcttt aaaaaggata atttcattgc ttgggatgac    840
aaagtctatc catcaatttt gaattttggt gcaccacttc ccaagcctct tcctagaatt    900
gccccaaata atgctccact ggcaagattg ttcatcgaat ttctatatta ctactcgatg    960
ttcaacttca agaaaaacta cattggtgcc aggcctgtaa tggtcatgga tcgaagaaca   1020
tcacaaaaca atatggttcg tagttcaaca aacaaagagg tgtgtattca agatccattc   1080
gatgagcaca acccgggaag aactgtaaga acattgaata gaattaaaga tgttatgaga   1140
agcacatatc agaagtttct ccctgtcgaa ggctccgaat tcacgtttcc tacactagat   1200
gatattatca atatgtcacc agaagtgcct aaaccatcgc gtgcagaagt tcgaaacttc   1260
cgagctgaag ccacagaagt gaatcgagtc ggcttaggtg tctactgtcg gaactcattt   1320
gtatag                                                              1326
```

<210> SEQ ID NO 53
<211> LENGTH: 441
<212> TYPE: PRT
<213> ORGANISM: Caenorhabditis elegans

<400> SEQUENCE: 53

```
Met Ser Gln Pro Asn Lys Asp Gln Arg Ser Pro Glu Asp Ile Asp Phe
1               5                   10                  15

Lys Val Lys Ala Asn Pro Lys Ala Phe His Lys Phe Asn Gly Lys Phe
            20                  25                  30

Gln Arg Val Leu Arg Asp His Glu Asp Phe Asn Ile Leu Ser Ile
        35                  40                  45

Ser Met Gln Asp His Phe Asp Thr Thr Lys Gln Pro Lys Glu Glu Phe
    50                  55                  60

Gly Lys Lys Met Asp Trp Cys Tyr Gln Leu Lys Asn Ile Ile Ser Lys
65                  70                  75                  80

Asn Asn Pro Thr Trp Leu Phe Asn Ile Val Pro Thr Gly Ser Thr Val
                85                  90                  95

Thr Gly Leu Ala Thr Lys Asn Ser Asp Leu Asp Val Ala Ile His Ile
            100                 105                 110

Pro Gln Ala Ala Arg Val Leu Glu Gln Glu Glu Arg Gly Arg Asn Ile
        115                 120                 125

Thr Asp Asp Glu Arg Gln Ala Ser Trp Arg Ile Gln Leu Glu Ile
    130                 135                 140

Leu Gln Ile Val Arg Leu Asn Leu Gln Asn Asp Glu Gln Ile Asn Ser
145                 150                 155                 160

Arg Ile Asn Trp Glu His Gly Ile Gln Leu Val Gln Ala Gln Ile Gln
                165                 170                 175
```

```
Ile Leu Lys Val Met Thr Val Asp Gly Ile Asp Cys Asp Ile Ser Val
            180                 185                 190

Val Met Asp Arg Phe Leu Ser Ser Met His Asn Ser Phe Leu Ile Arg
        195                 200                 205

His Leu Ala His Ile Asp Gly Arg Phe Ala Pro Leu Cys Ala Ile Val
    210                 215                 220

Lys Gln Trp Ala Ala Ser Thr Lys Val Lys Asp Pro Lys Asp Gly Gly
225                 230                 235                 240

Phe Asn Ser Tyr Ala Leu Val Leu Leu Val Ile His Phe Leu Gln Cys
                245                 250                 255

Gly Thr Phe Pro Pro Ile Leu Pro Asn Leu Gln Glu Ile Phe Lys Lys
            260                 265                 270

Asp Asn Phe Ile Ala Trp Asp Asp Lys Val Tyr Pro Ser Ile Leu Asn
        275                 280                 285

Phe Gly Ala Pro Leu Pro Lys Pro Leu Pro Arg Ile Ala Pro Asn Asn
290                 295                 300

Ala Pro Leu Ala Arg Leu Phe Ile Glu Phe Leu Tyr Tyr Tyr Ser Met
305                 310                 315                 320

Phe Asn Phe Lys Glu Asn Tyr Ile Gly Ala Arg Pro Val Met Val Met
                325                 330                 335

Asp Arg Arg Thr Ser Gln Asn Asn Met Val Arg Ser Ser Thr Asn Lys
            340                 345                 350

Glu Val Cys Ile Gln Asp Pro Phe Asp Glu His Asn Pro Gly Arg Thr
                355                 360                 365

Val Arg Thr Leu Asn Arg Ile Lys Asp Val Met Arg Ser Thr Tyr Gln
            370                 375                 380

Lys Phe Leu Pro Val Glu Gly Ser Glu Phe Thr Phe Pro Thr Leu Asp
385                 390                 395                 400

Asp Ile Ile Asn Met Ser Pro Glu Val Pro Lys Pro Ser Arg Ala Glu
                405                 410                 415

Val Arg Asn Phe Arg Ala Glu Ala Thr Glu Val Asn Arg Val Gly Leu
                420                 425                 430

Gly Val Tyr Cys Arg Asn Ser Phe Val
            435                 440

<210> SEQ ID NO 54
<211> LENGTH: 87
<212> TYPE: RNA
<213> ORGANISM: Artificial Sequence
<220> FEATURE:
<223> OTHER INFORMATION: synthetic sequence

<400> SEQUENCE: 54
ggcaacuugg ccgagugguu aaggcgaaag auuagaaauc uuuacaugag gaucacccau    60
gugcagguuc gaguccugca guugucg                                       87
```

US 10,301,605 B2

POLY(UG) POLYMERASE, CONSTRUCTS, AND METHODS OF MAKING AND USING THE SAME

CROSS-REFERENCE TO RELATED APPLICATIONS

This application claims benefit of U.S. Provisional Patent Application 62/084,739 filed Nov. 26, 2014.

STATEMENT REGARDING FEDERALLY SPONSORED RESEARCH

This invention was made with government support under GM050942 awarded by the National Institutes of Health. The government has certain rights in the invention.

BACKGROUND OF THE INVENTION

This invention relates to ribonucleotidyl transferase. Specifically, this invention relates to a poly(UG) polymerase.

Ribonucleotidyl transferases (NTases) are known to add nucleotides to the ends of RNAs. Presently, there are only a few classes of known NTases, specifically, poly(A) polymerases, poly(U) polymerases, CCA-adding enzymes, and noncanonical poly(A) polymerases. However, given the vast number of possible nucleotide combinations that could be added to the ends of RNAs, the number of known NTases is quite small.

A need exists for new NTases and corresponding constructs, compositions of matter, methods, and uses.

SUMMARY OF THE INVENTION

The present invention overcomes the aforementioned drawbacks by providing kits, compositions of matter, and methods as described herein.

In one embodiment, this disclosure provides a method for adding a poly(UG) sequence to the end of an RNA substrate. The method can include one or more of the following steps: contacting the RNA substrate with a poly(UG) polymerase; and allowing the poly(UG) polymerase to add a poly(UG) sequence to the end of the RNA substrate by retaining contact between the RNA substrate and the poly(UG) polymerase for a period of time from about 1 second to about 28 days. In preferred embodiments, the poly(UG) polymerase is *Caenorhabditis elegans* RDE-3.

In another embodiment, this disclosure provides a construct. The construct can include a poly(UG) polymerase activity sequence linked to a heterologous promoter.

In yet another embodiment, this disclosure provides a fusion protein. The fusion protein can include a poly(UG) polymerase activity domain and an RNA-interaction domain.

In a further embodiment, this disclosure provides a method for identifying a ribonucleotidyl transferase. The method can include one or more of the following steps: identifying a candidate enzyme having a ribonucleotidyl-transferase activity domain; tethering the candidate enzyme to a reporter RNA substrate resulting in a potentially tailed RNA substrate; and sequencing the potentially tailed RNA substrate to identify the presence or absence of the polynucleotide tail, wherein the presence of the polynucleotide tail indicates that the candidate enzyme is a ribonucleotidyl transferase. In certain embodiments, the tethering step can include fusing a binding domain to the candidate enzyme and inserting an RNA sequence to which the binding domain binds within the reporter RNA substrate.

In another embodiment, this disclosure provides a kit for adding a poly(UG) tail to an RNA substrate. The kit can include the following: a poly(UG) polymerase or a means of expressing a poly(UG) polymerase in a cellular environment; and one or more reagents for providing reaction conditions enabling the poly(UG) polymerase to add the poly(UG) tail to the RNA substrate.

In yet another embodiment, this disclosure provides a method of synthesizing cDNA of an RNA of unknown sequence. The method can include the following: contacting the RNA of unknown sequence with a poly(UG) polymerase for a length of time sufficient to introduce a poly(UG) tail to a 3' end of the RNA of unknown sequence; and priming a cDNA synthesis with a poly(CA) primer.

In a further embodiment, this disclosure provides a method of synthesizing cDNA of an RNA of unknown sequence. The method can include the following: contacting the RNA of unknown sequence with a poly(UG) polymerase for a first length of time sufficient to introduce a poly(UG) tail to a 3' end of the RNA of unknown sequence, the poly(UG) tail having a length sufficient to form a hairpin due to interaction of a 5' portion of the poly(UG) tail with a 3' portion of the poly(UG) tail; waiting a second length of time sufficient to allow formation of the hairpin; and priming a cDNA or cRNA synthesis with the poly(UG) tail as a primer.

In another embodiment, this disclosure provides a purified preparation of a poly(UG) polymerase, preferably at least 95% pure.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS AND EXHIBITS

The patent or application file contains at least one drawing executed in color. Copies of this patent or patent application publication with color drawing(s) will be provided by the Office upon request and payment of the necessary fee.

FIG. 1A is a schematic representation of a heterologous method of identifying a ribonucleotidyl transferase by expression in *S. cerevisiae*, in accordance with the present disclosure.

FIG. 1B outlines the experimental procedure to prepare tailed reporter tRNA for high throughput sequencing analysis.

FIG. 1C outlines the steps of computational processing of the high throughput sequencing data to determine the sequence of the tails added to the reporter tRNA, and gives an example of the results as shown by a graph depicting PUP-2 poly(U) polymerase activity.

FIG. 2 is a summary of the NTases from six different species and their resulting activities as assayed by the heterologous method depicted in FIG. 1.

FIG. 4 shows representative tail sequences of Example 1.

Figure 9:
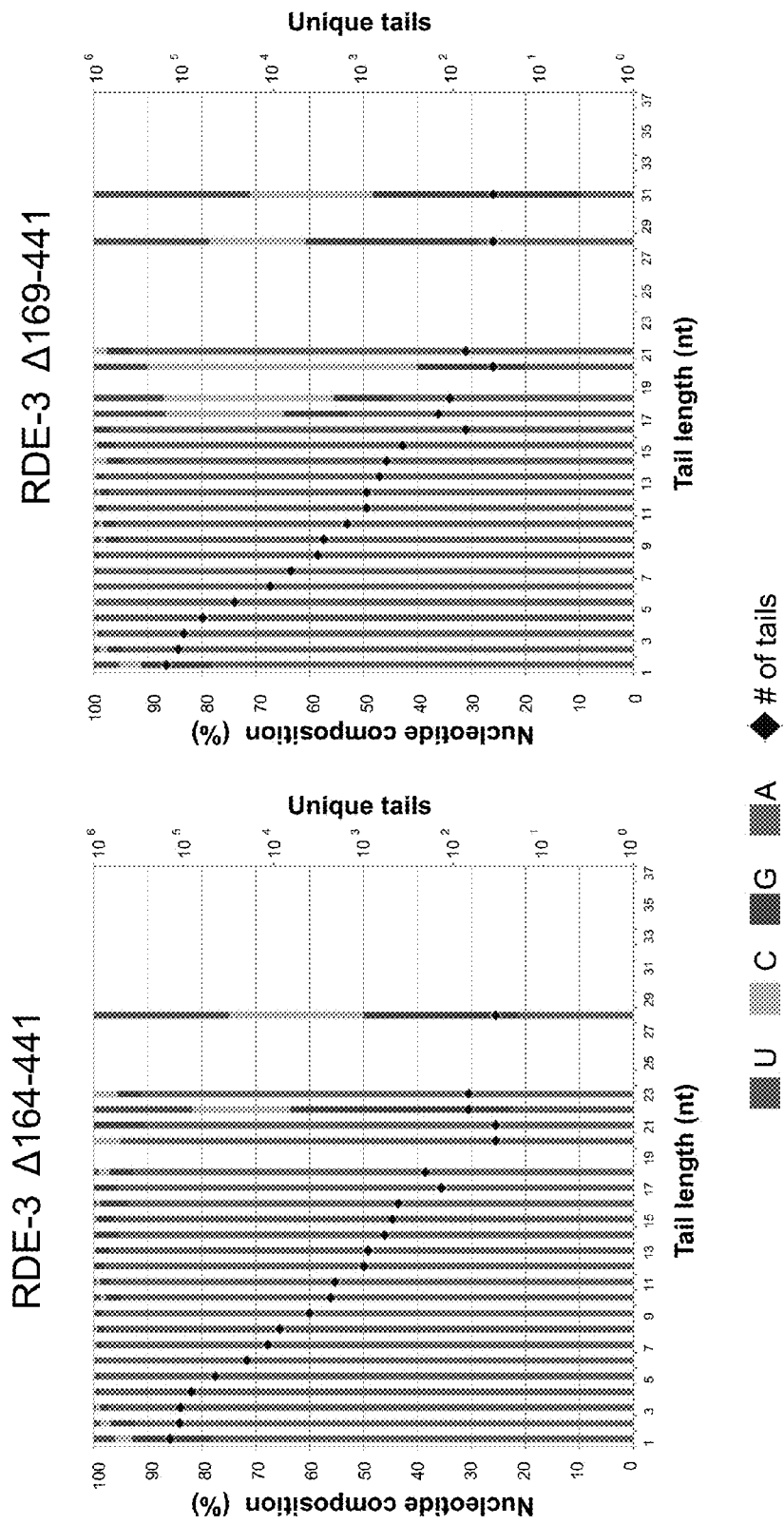

FIG. 9 shows a lack of poly(UG) tailing activity in RDE-3 with an in-frame deletion from residue 164 to residue 441 and an RDE-3 with an in-frame deletion from residue 169 to residue 441.

Figure 10:
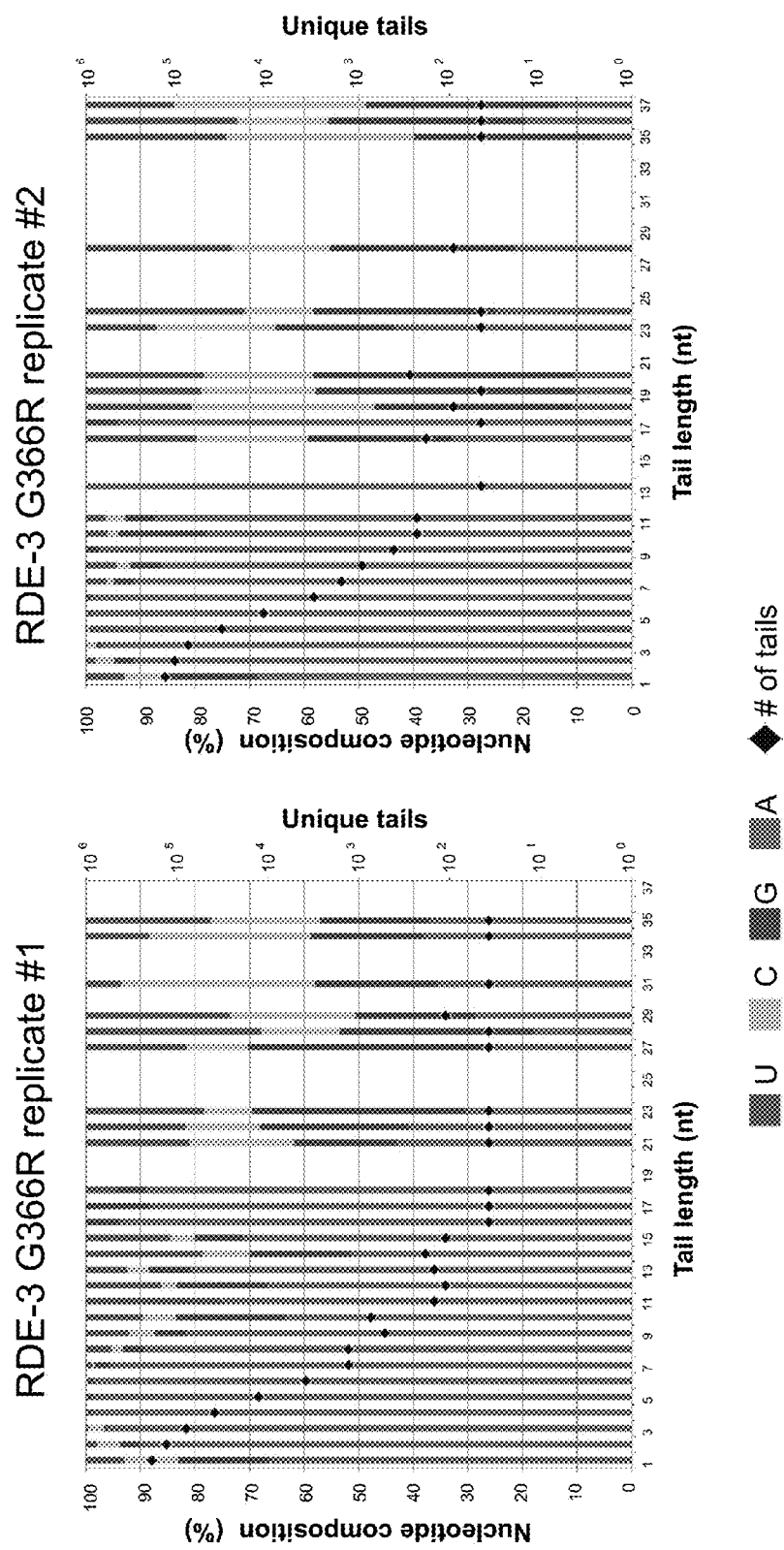

FIG. 10 shows reduced poly(UG) tailing activity in two biological replicates of G366R-modified RDE-3.

FIG. 11 is a summary of the effects of various mutations on the poly(UG) polymerase activity of RDE-3.

Figure 12A:
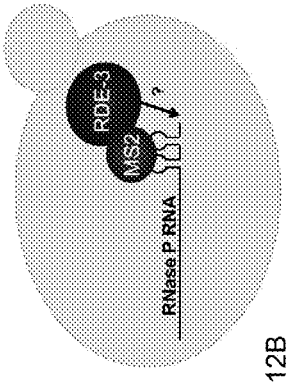

FIG. 12A shows the procedure used to measure RDE-3 poly(UG) polymerase activity on RNase P RNA reporter in *S. cerevisiae*.

Figure 12B:
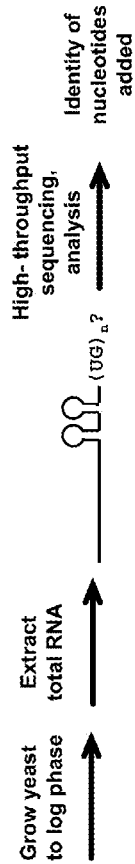

FIG. 12B shows representative tail sequences from three biological replicates resulting from RDE-3 poly(UG) polymerase activity on the RNase P RNA reporter.

Figures 13A, 13B, 13C:
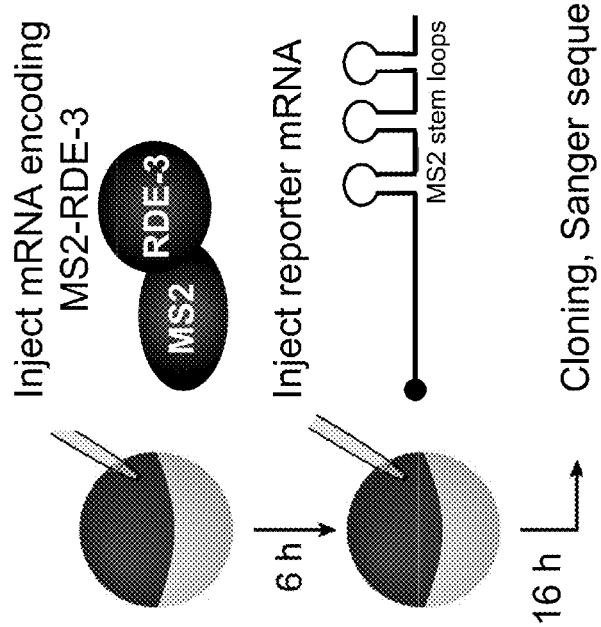

FIG. 13A shows the procedure used to test RDE-3 poly (UG) polymerase activity in *X. laevis* oocytes.

FIG. 13B shows the resulting tail sequences of the poly (UG)-tailed reporter RNAs from two biological replicates of Example 4 produced in *X. laevis*, an additional non-native organism.

Figure 14:
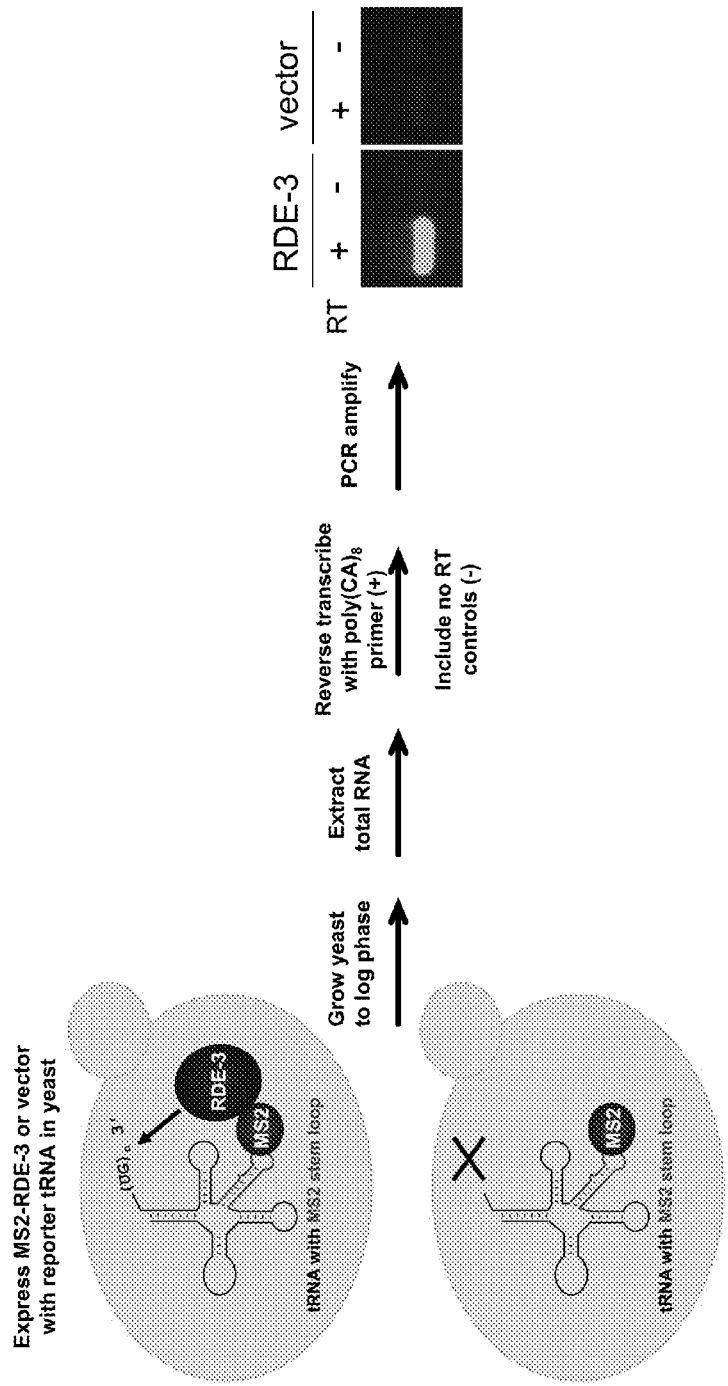

FIG. 14 shows that a poly(CA)$_8$ primer can be used to prime reverse transcription of a poly(UG)-tailed tRNA reporter (Example 5), but not a tRNA reporter lacking a poly(UG) tail.

FIG. 15 contains the DNA sequence that encodes RDE-3 isoform a and the protein sequence of RDE-3 isoform a.

DETAILED DESCRIPTION OF THE INVENTION

In General

In one embodiment, the present invention is a new ribonucleotidyl transferase, namely a poly(UG) polymerase. Also disclosed are constructs, methods, and uses relating to the same. In a preferred embodiment, one would contact an RNA substrate with the new poly(UG) polymerase to add a poly(UG) tail to the RNA substrate. Examples below show that RDE-3 has been shown to possess poly(UG) polymerase activity.

In a preferred embodiment, the poly(UG) polymerase adds a poly(UG) tail having a sequence of UG-repeating units, such as UGUG, UGUGUG, UGUGUGUG, or GUGU, GUGUGU, GUGUGUGU, and the like, to an RNA substrate. Examples below show that the majority of poly(UG) tails added by a RDE-3/MS2 coat protein chimera have a UG-repeating sequence of between 4 and 50 residues.

In another embodiment, the poly(UG) polymerase linked to a heterologous promoter can form a construct that expresses a poly(UG) polymerase activity domain fused to an RNA-interaction domain as a fusion protein.

In another embodiment, when coupled with high-throughput sequencing or TOPO® cloning and Sanger sequencing, the methods of the present invention allow the unbiased analysis of the sequence of an unknown tail that is added by a ribonucleotidyl transferase to a reporter RNA in both in vivo and in vitro situations.

In order to identify unknown ribonucleotidyl transferases that can add tails having an unknown sequence, the present invention also provides a method for identifying a ribonucleotidyl transferase. This method involves, in general, the following steps: 1) locate a candidate enzyme having a ribonucleotidyl transferase domain, 2) fuse the candidate enzyme to an RNA-interaction domain resulting in a fusion protein, 3) contact an RNA substrate with the fusion protein resulting in a potentially tailed RNA substrate, and 4) sequence the potentially tailed RNA substrate to identify the presence or absence of the polynucleotide tail. The presence of the polynucleotide tail can indicate that the candidate enzyme is a ribonucleotidyl transferase.

Definitions

As used herein, a ribonucleotidyl transferase "activity sequence" is a nucleotide sequence that codes a protein domain containing ribonucleotidyl transferase activity. Expression of a ribonucleotidyl transferase activity sequence results in a ribonucleotidyl transferase activity domain.

As used herein, a "poly(UG) sequence" is an alternating sequence of U and G residues of at least 4 residues. There is no requirement that the sequences start with either a U or G residue. Either residue is correct.

As used herein, a ribonucleotidyl transferase "activity domain" is a protein domain containing ribonucleotidyl transferase activity. A ribonucleotidyl transferase activity domain results from expression of a ribonucleotidyl transferase activity sequence.

As used herein, a "modified" nucleotide is any nucleotide containing within it a naturally occurring nucleotide, possibly with additional modifications not found in the naturally-occurring nucleotide. For example, a modified uridine contains the structure of naturally-occurring uridine along with other modifications, such as biotinylation.

Methods of the Present Invention

In one embodiment, the present invention provides a method for adding a poly(UG) sequence to the end of an RNA substrate. The method typically comprises contacting the RNA substrate with a poly(UG) polymerase, which can involve tethering the poly(UG) polymerase to the RNA substrate. The poly(UG) polymerase will add a poly(UG) sequence to the end of the RNA substrate if contact is retained between the RNA substrate and the poly(UG) polymerase for a period of time from about 1 second to about 28 days, including, but not limited to, a period of time from about 10 seconds to about 14 days, from about 1 minute to about 7 days, from about 5 minutes to about 1 day, or from about 10 minutes to about 24 hours. In certain embodiments, the poly(UG) polymerase will add a poly (UG) sequence to the end of the RNA substrate if the poly(UG) polymerase is expressed in the presence of the RNA substrate for a period of time from about 10 seconds to about 28 days, including, but not limited to, a period of time from about 20 seconds to about 14 days, from about 1 minute to about 7 days, from about 5 minutes to about 1 day, or from about 10 minutes to about 24 hours. In certain embodiments, the method can be performed in vitro.

In certain embodiments, the poly(UG) polymerase can be *C. elegans* RDE-3. In certain embodiments, the poly(UG) polymerase can include at least a portion of NCBI Reference Sequence NP_491834.1. In certain embodiments, the poly (UG) polymerase can include at least 5%, at least 10%, at least 25%, at least 50%, at least 60%, at least 70%, at least 80%, at least 90%, at least 95%, at least 99%, or about 100% of NCBI Reference Sequence NP_491834.1. It should be appreciated that the methods disclosed herein can suitably be performed with poly(UG) polymerases from other sources.

In certain embodiments, the poly(UG) polymerase can be a fusion protein including a poly(UG) polymerase activity domain and an RNA-interaction domain.

As described above, the fusion protein includes a poly(UG) polymerase activity domain. In certain embodiments, the poly(UG) polymerase activity domain can comprise poly(UG) polymerases, such as C. elegans RDE-3, and the like. In certain embodiments, the poly(UG) polymerase activity domain can include at least a portion of NCBI Reference Sequence NP_491834.1 (see FIG. 15). In certain embodiments, the poly(UG) polymerase activity domain can include GSTVTGLATKNSDLDV. The fusion protein disclosed herein can suitably contain poly(UG) polymerase activity domains from other sources.

In certain embodiments, the poly(UG) tail can include unmodified nucleotides. In certain embodiments, the poly(UG) tail can include uridine, polyuridine, guanosine, or polyguanosine.

In certain embodiments, the poly(UG) sequence can include modified nucleotides. Many modified nucleotide analogs exist and have proven useful for many biological and biochemical applications. The descriptions herein focus on uridine analogs, but many of the modifications described herein are available for the other nucleotides. The modified nucleotides would be added to the in vitro or in vivo reactions, and enable the investigator to purify the RNAs that have received tails. Analogs include 4-thiouridine and click-functionalized nucleotide analogs (available commercially from Jena Bioscience, Jena, Germany). These are nucleotides that have highly reactive groups attached to them that enable easy attachment of other molecules. For example, they enable the easy attachment of biotin to the modified nucleotide. This class of analog allows both of the experiments described above.

The fusion proteins described herein can be prepared by fusing an RNA interaction domain to the poly(UG) polymerase activity domain at the C-terminus or the N-terminus, preferably via recombinant DNA techniques. In an exemplary embodiment, an MS2 coat protein can be fused to the N-terminus of RDE-3 and an RGS-H6 epitope tag can be fused to the RDE-3 C-terminus. In another example, three HA epitope tags and an MS2 coat protein can be fused to the N-terminus of RDE-3 and an RGS-H6 epitope tag can be fused to the RDE-3 C-terminus.

The present invention may include a means for expressing a fusion protein within the cellular environment. This expression means can include methods known to those having ordinary skill in the art. In certain embodiments, the means can include an mRNA that encodes the expression of the fusion protein that is suitable for microinjection into a cell of interest, a plasmid or other vector coding expression of the fusion protein that is suitable for insertion into the DNA of a cell of interest, a purified recombinant protein injected into a cell, or strains containing the plasmid of the fusion protein without requiring genomic integration (i.e., transfections in cell lines), or a combination thereof.

Methods of expressing a fusion protein within the cellular environment can include many methods known to those having ordinary skill in the art. In certain embodiments, the expression can include microinjecting an mRNA encoding the expression of the fusion protein into a cell of interest, inserting a plasmid or other vector encoding expression of the fusion protein into the cell of interest, or a combination thereof. In embodiments where the means of expressing or the expressing step include a plasmid, the plasmid can include a DNA sequence encoding expression of the fusion protein and the plasmid can be adapted for insertion into the DNA of the cell of interest at a position where it replaces the exogenous DNA coding the RNA-interaction domain. In certain embodiments, the plasmid can be created using a base plasmid or vector that includes coding for the poly(UG) polymerase activity domain. In certain embodiments, the plasmid can include at least a portion of NCBI Reference Sequence NM_059433.7.

This disclosure also provides an assay that can identify ribonucleotidyl transferase activity and which can identify the sequence of nucleotides that are added by a ribonucleotidyl transferase. The assay can be a method for identifying a ribonucleotidyl transferase. The method typically comprises identifying a candidate enzyme having a ribonucleotidyl transferase activity domain. One would tether the candidate enzyme to a reporter RNA substrate resulting in a potentially tailed RNA substrate. To accomplish this, one may fuse a binding domain to the candidate enzyme and insert an RNA sequence to which the binding domain binds within the reporter RNA substrate. To identify the presence or absence of the polynucleotide tail, one would sequence the potentially tailed RNA substrate. The presence of the polynucleotide tail would indicate that the candidate enzyme is a ribonucleotidyl transferase.

In certain embodiments, a ribonucleotidyl transferase activity domain can be $GSx_{7-13} DhDh$, where $x_{7-43}$ can be any 7-13 amino acid residues and h is a hydrophobic residue. In a preferred embodiment, the ribonucleotidyl transferase activity domain can include GSTVTGLATKNSDLDV (SEQ ID NO:37).

Referring to FIG. 1A, a schematic view of the procedure for expressing a candidate NTase in the yeast S. cerevisiae and tethering this enzyme to a reporter tRNA to measure in vivo tailing activity. Referring to FIG. 1B, one aspect of the invention is shown where an unknown tail that has been added to the 3' end of a reporter RNA in vivo is processed for unbiased analyses of the tail sequences. An adapter of known sequence containing a random heptamer is added to the 3' end of the unknown tail, reverse transcription is performed with the adapter primer, PCR is performed on the resulting cDNA, and the unknown tail is sequenced either by high-throughput sequencing or by TOPO® cloning (available from Life Technologies, Carlsbad, Calif.) and Sanger sequencing. Following high-throughput sequencing, the tail sequence and random heptamer are computationally extracted (FIG. 1C), PCR duplicates are removed using the random heptamer, and the tail length, tail nucleotide composition, and tail abundance are quantified. The method depicted in FIG. 1 can be applied to determine nucleotide specificities of known and new NTases from potentially any organism. Thus far, thirty-four NTases have been tested from six different species. Their names and nucleotide tailing activities are summarized in FIG. 2.

This disclosure also provides a method of synthesizing cDNA of an RNA of unknown sequence. In certain embodiments, the method includes using a poly(CA) primer or an intramolecular primer.

In certain embodiments, the method includes contacting the RNA of unknown sequence with a poly(UG) polymerase for a length of time sufficient to introduce a poly(UG) tail to a 3' end of the RNA of unknown sequence and priming a cDNA synthesis with a poly(CA) primer.

In certain embodiments, the method includes contacting the RNA of unknown sequence with a poly(UG) polymerase for a first length of time sufficient to introduce a poly(UG) tail to a 3' end of the RNA of unknown sequence, the poly(UG) tail having a length sufficient to form a hairpin due to interaction of a 5' portion of the poly(UG) tail with a 3' portion of the poly(UG) tail to form an intramolecular primer, waiting a second length of time sufficient to allow formation of the hairpin, and priming a cDNA synthesis with the poly(UG) tail as a primer.

Applications of Poly(UG) Polymerase

The kits, compositions of matter, and methods described herein have many applications to biological problems that are currently difficult or nearly impossible to address.

First, as demonstrated by the prophetic example utilizing a poly(CA) DNA primer described herein, poly(UG) polymerases are capable of identifying RNAs of unknown sequence by using a poly(CA) DNA primer.

Second, as demonstrated by the prophetic example utilizing an intramolecular primer described herein, poly(UG) polymerases are capable of identifying RNAs of unknown sequence by using an intramolecular primer formed by a poly(UG) hairpin.

Third, as an alternative to conventional 3' RACE, a UG tail added by a poly(UG) polymerase can be used to sequence 3' ends of RNAs that lack a poly(A) tail.

Fourth, poly(UG) polymerases can be used to label 3' ends of RNAs with a defined sequence or with modified nucleotides.

Kits of the Present Invention

This disclosure provides a kit for adding a poly(UG) tail to an RNA substrate. The kit can include a poly(UG) polymerase or a means of expressing a poly(UG) polymerase in a cellular environment and one or more reagents for providing reaction conditions enabling the poly(UG) polymerase to add the poly(UG) tail to the RNA substrate. The one or more reagents can be selected from reagents disclosed herein.

Compositions of Matter of the Present Invention

This disclosure provides compositions of matter including constructs and fusion proteins.

In certain embodiments, the construct can include a poly(UG) polymerase activity sequence, preferably linked to a heterologous promoter.

The poly(UG) polymerase activity sequence can be expressed as *C. elegans* RDE-3. In certain embodiments, the poly(UG) polymerase activity sequence can include at least a portion of NCBI Reference Sequence NM_059433.7 (see FIG. 15). In certain embodiments, the poly(UG) polymerase activity sequence can include at least 5%, at least 10%, at least 25%, at least 50%, at least 60%, at least 70%, at least 80%, at least 90%, at least 95%, at least 99%, or about 100% of NCBI Reference Sequence NM_059433.7.

The heterologous promoter can be selected from any promoter from a species that is different than the species to which the poly(UG) polymerase activity sequence is native.

In certain embodiments, the fusion protein can include a poly(UG) polymerase activity domain and an RNA-interaction domain, as described above.

In certain embodiments, the present invention is an at least partially purified preparation of poly(UG) polymerase. Preferably, the preparation is at least 95% pure.

EXAMPLES

Example 1. Poly(UG) Polymerase Activity of RDE-3

The yeast *S. cerevisiae* was used to develop a new system to detect the activity of previously uncharacterized ribonucleotidyl transferases (NTases) by tethering an MS2 fusion of the candidate enzyme to a novel reporter tRNA modified to contain an MS2 stem loop and then sequencing the added tails. The class II serine tRNA with an AGA anticodon was used as a base for the reporter tRNA. The variable stem loop of the tRNA was replaced with an MS2 stem loop, resulting in the following sequence of the mature tRNA: 5' GGCAACUUGGCCGAGUGGUUAAGGC-GAAAGAUUAGAAAUCUUUACAUGAGGAUCAC-CCAUG UGCAGGUUCGAGUCCUGCAGUUGUCG 3' (SEQ ID NO:54). Class II tRNAs are ideal candidates to use as reporter tRNAs because their variable stem loop structure is similar to an MS2 stem loop. However, any tRNA could be used as a reporter, as long as the MS2 stem loop is placed in a region that does not affect the post-transcriptional processing of the tRNA.

BY4741 yeast strains expressing both the reporter tRNA and RDE-3 fused to MS2 coat protein (MS2) were grown to log phase (OD=0.8-1.0) in synthetic media lacking uracil and leucine to select for the presence of the desired plasmids. The MS2-RDE-3 fusion protein bound to the MS2 stem loop and attached an unknown tail to the 3' end of the reporter tRNA. Total RNA, including the reporter tRNA having an unknown tail, was isolated by lysis of yeast with acid-washed beads followed by phenol-chloroform extraction and ethanol precipitation. The RNA was treated with TURBOT" DNase (available from Ambion/ThermoFisher Scientific, Waltham, Mass.) to remove contaminating DNA, and the RNA was purified by using an RNA extraction kit (available from ThermoFisher Scientific, Waltham, Mass.). Total RNA was ligated with a 5' adenylated adapter containing a 5'-terminal random heptamer and a 3' dideoxycytidine (5' AppNNNNNNN TGGAATTCTCGGGTGC-CAAGG ddC 3' SEQ ID NO:38), which prevents ligation of multiple adapters onto the same RNA molecule, by using T4 RNA ligase 2, truncated KQ (available from New England Biolabs, Ipswich, Mass.). The adapter-modified reporter RNA was reverse transcribed with the ImProm-II™ reverse transcription system (available from Promega, Madison, Wis.) using a primer complementary to the adapter sequence (5' GCCTTGGCACCCGAGAATTCCA 3' SEQ ID NO:39). The resulting cDNA was PCR amplified using a 5' primer containing a sequence specific for the tRNA reporter (5' GAGGATCACCCATGTCGCAG 3' SEQ ID NO:40) and a 3' primer containing sequence complementarity to the adapter sequence. Biological replicates were produced by repeating the tethered function assay two to five times.

PCR products resulting from one of the biological replicates underwent TOPO® cloning according to manufacturer's instructions (available from ThermoFisher Scientific, Waltham, Mass.) and Sanger sequencing. The following tail sequences were found: CCA+GUGUGU, CCA+UGUGU-GUGUGUGUG (SEQ ID NO:41), and CC+GUGUGU-GUGUGUGU (SEQ ID NO:42). The CCA-tail, and partial CCA-tails (C and CC), also observed in high-throughput sequencing data described below, are believed to be the result of normal cellular tailing activity, so these tail sequences indicated that the reporter RNA was tailed with UG-rich tails.

Figure 3:
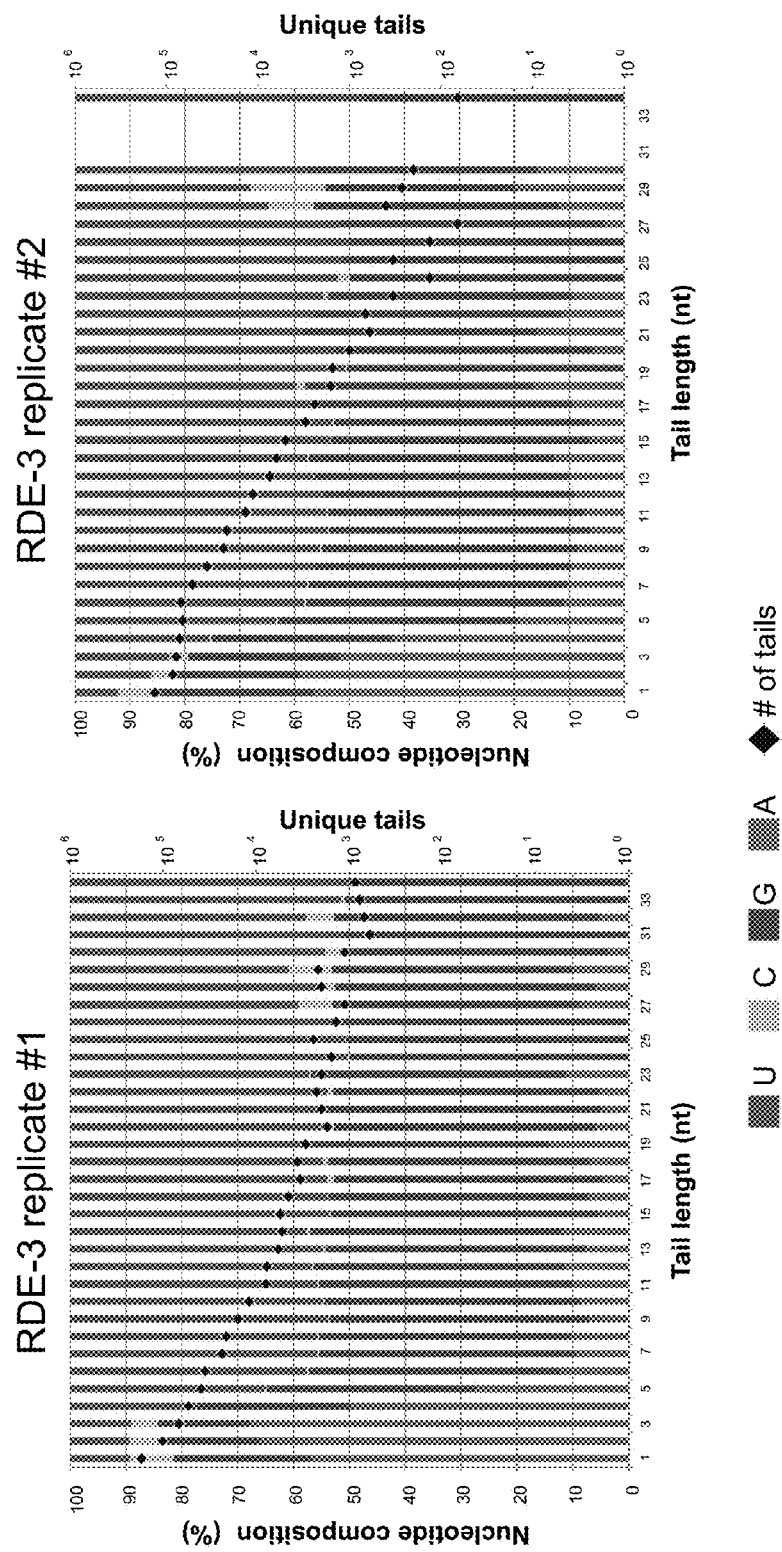
FIG. 3 shows plots of percent nucleotide composition and number of unique tails as a function of tail length of Example 1 showing poly(UG) polymerase activity by RDE-3.

All biological replicates underwent high-throughput sequencing to identify the sequences of tails added to the reporter RNA. To generate PCR products compatible with Illumina® sequencing platforms, appropriate sequences to allow for binding of DNA fragments to the sequencing flow cell were added to the 5' and 3' PCR primers described above (5' primer: 5' AATGATACGGCGACCACCGAGATCTA-CACGTTCAGAGTTCTACAGTCCGACGATCGAG- GATC ACCCATGTCGCAG 3' SEQ ID NO:43 and 3' primer: 5' CAAAGCAGAAGACGGCATACGAGAT SEQ ID NO:44-6 nt sample index-GTGACTGGAGTTCCTTG-GCACCCGAGAATTCCA 3' SEQ ID NO:45). Paired-end sequence reads were generated by sequencing the samples in the 5' and 3' directions on an Illumina® HiSeq® 2500 instrument. The resulting sequencing reads were processed using a custom Python script to perform the following steps. First, 5' and 3' adapter sequences were removed from the sequencing read. Then, the tRNA reporter-specific sequence was identified (5' GAGGATCACCCATGTCGCAGGTTC-GAGTCCTGCAGTTGTCGCCA 3' SEQ ID NO:46) to locate the end of the tRNA sequence and to identify the untemplated nucleotide tail added. Next, duplicate sequences resulting from PCR amplification (sequencing reads with identical tail sequence and identical random heptamer sequence) were discarded by requiring that a unique random heptamer sequence is associated with a tail of the same sequence. Finally, tail sequences were organized by length to measure abundance, and the composition of each nucleotide in the population was output as a percentage. The results for two biological replicates of wild-type RDE-3 are shown in FIGS. 3-4. Referring to FIG. 3, the percent nucleotide composition of the population and the number of unique tails (calculated as tails per million unique heptamers) as a function of tail length are plotted. For tail lengths of five and longer, the tails are dominated by the presence of U and G and the relative ratio is very close to 1:1. Referring to FIG. 4, some of the most abundant tail sequences are shown with their respective relative abundance. Strikingly, in most cases, the tail sequence is an alternating UG sequence. Overall, about 10% of the reporter sequences had tails containing UG repeats, and the remaining 90% of reporter sequences were largely not tailed.

Example 2. Mutations of RDE-3 to Alter Poly(UG) Polymerase Activity

Figure 5:
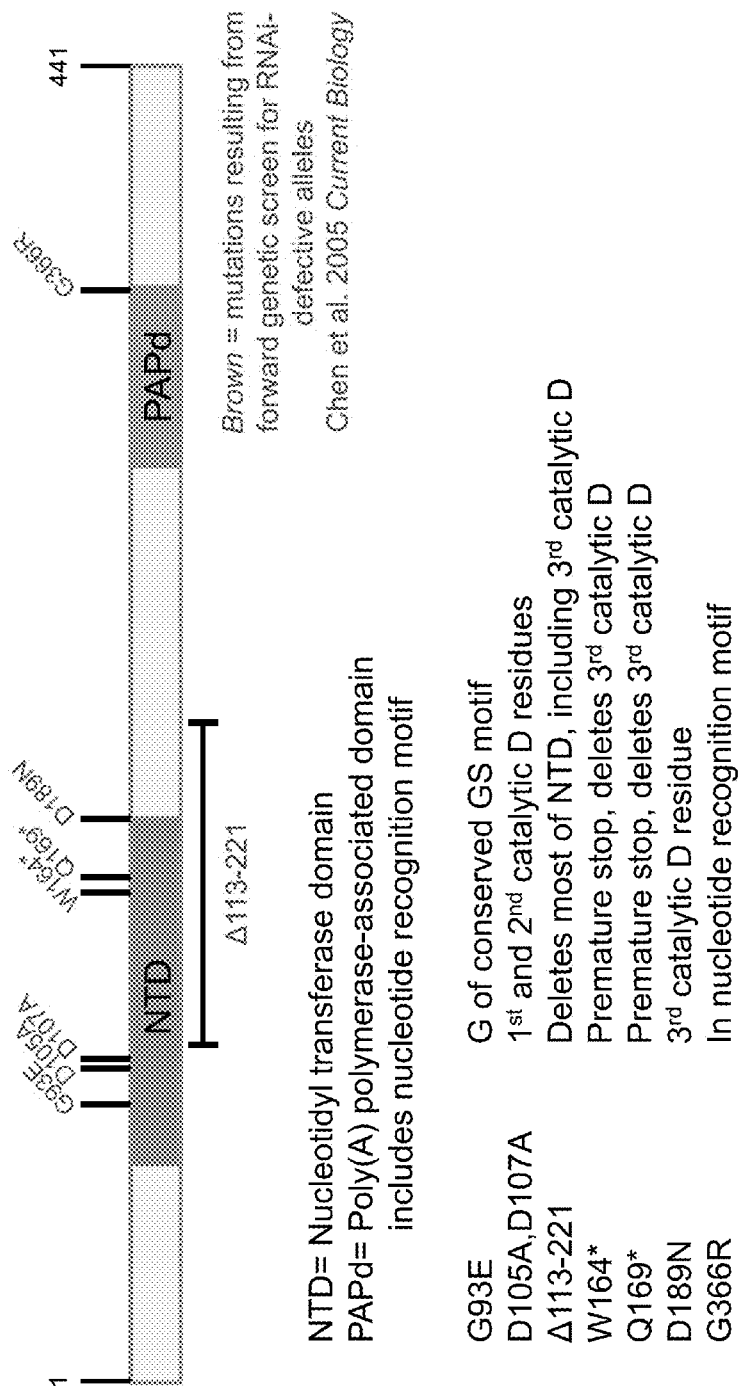
FIG. 5 is a schematic view of the RDE-3 protein sequence showing several mutations tested for poly(UG) polymerase activity.
Figure 6:
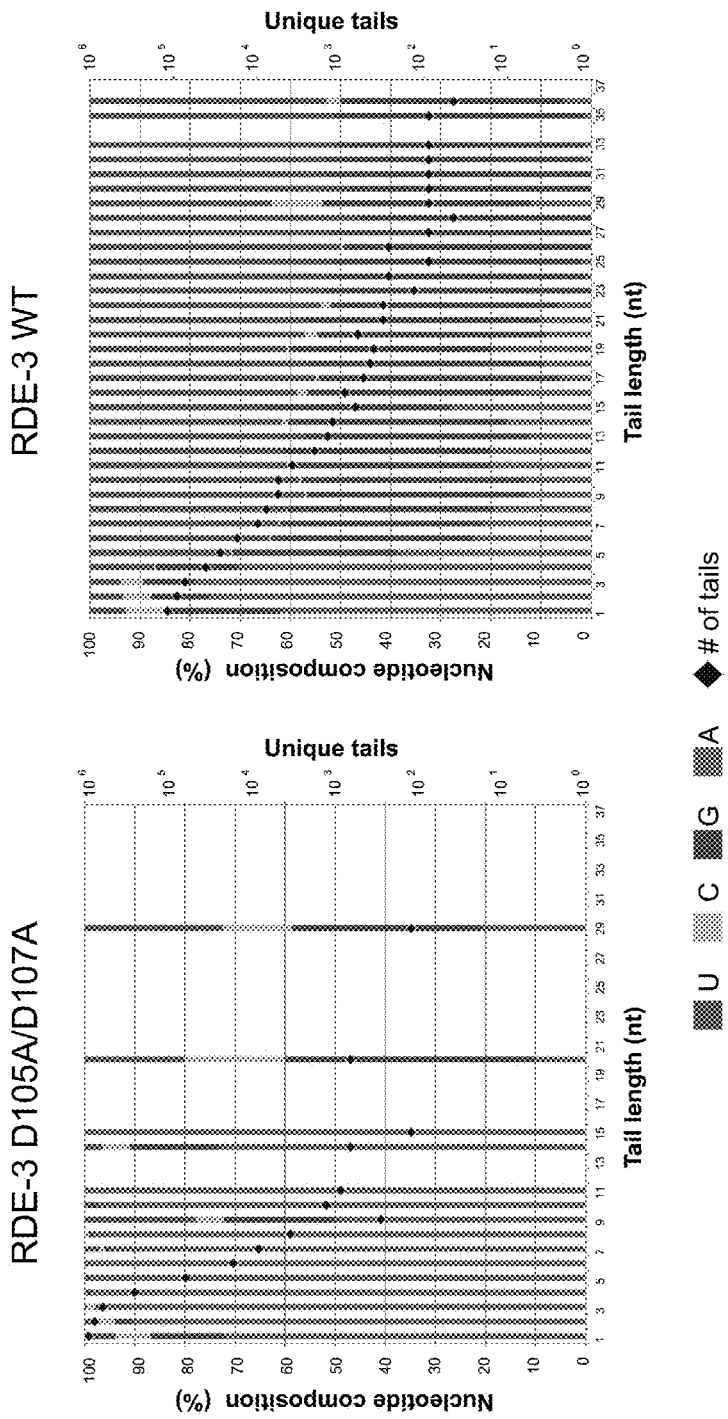
FIG. 6 shows a comparison of poly(UG) tailing activity of D105A- and D107A-modified RDE-3 compared with wild type.
Figure 7:
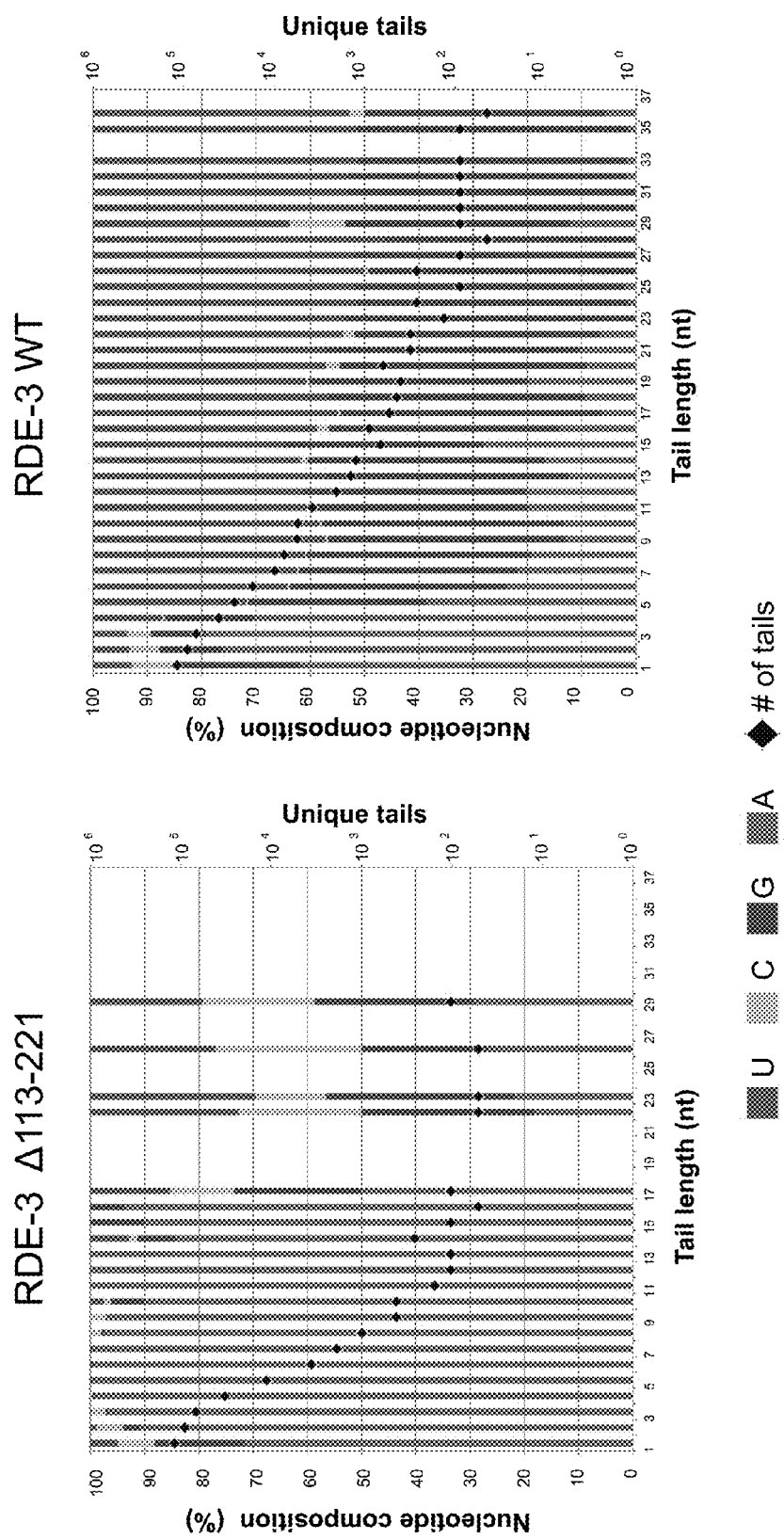
FIG. 7 shows a comparison of poly(UG) tailing activity of RDE-3 with an in-frame deletion from residue 113-221 compared with wild type.
Figure 8:
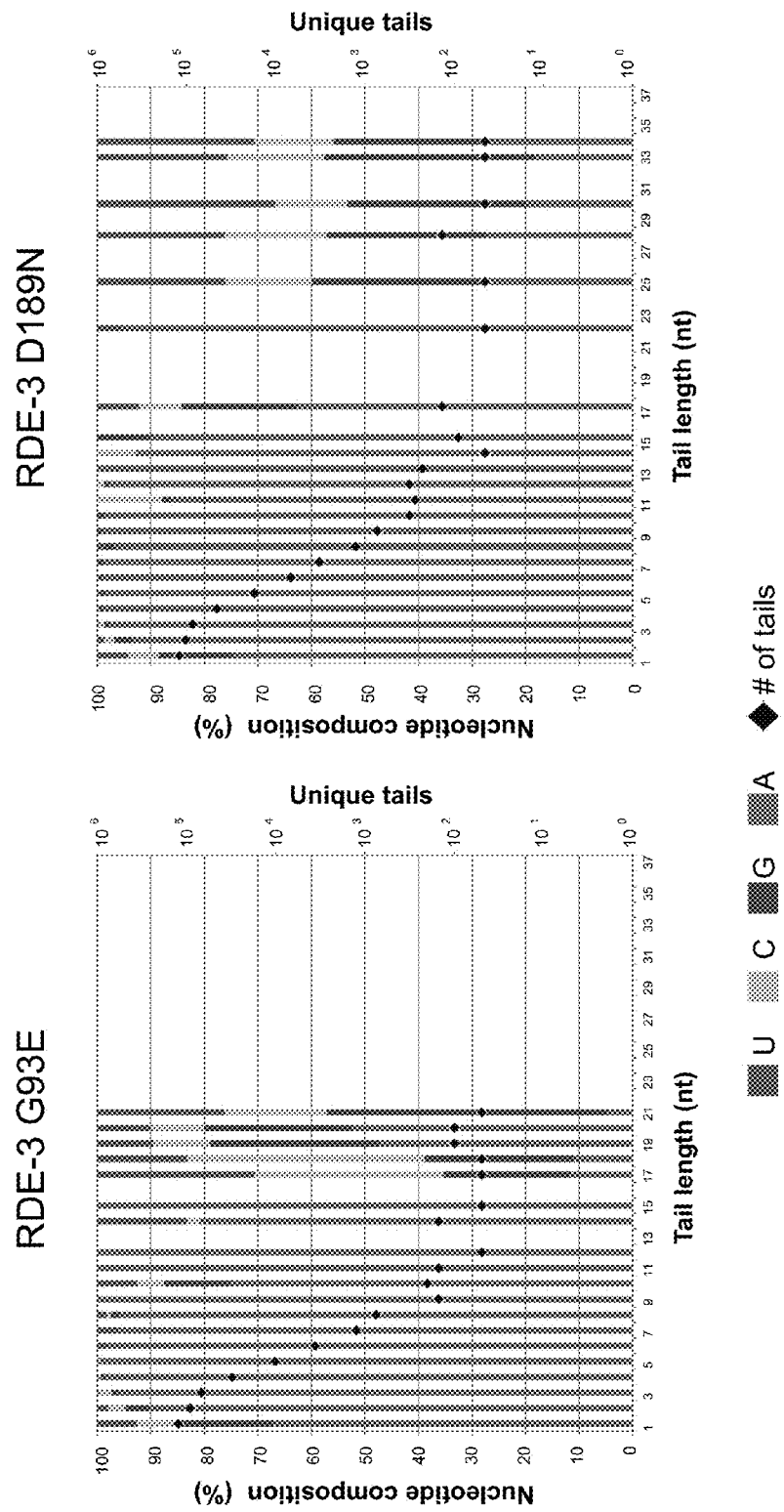
FIG. 8 shows a lack of poly(UG) tailing activity in G93E-modified RDE-3 and D189N-modified RDE-3.

FIG. 5 shows a schematic view of the RDE-3 protein sequence, including identification of the nucleotidyltransferase domain ("NTD"), the poly(A) polymerase-associated domain ("PAPd"), which includes a nucleotide recognition motif, the location of residues 113-221, and seven point mutations: five that were identified in Chen et al. (2005) and two modifying the first and second catalytic aspartic acid residues. The methods of Example 1 were repeated to express RDE-3 with the following mutations. FIG. 6 shows a comparison of the tailing activity of a D105A/D107A-modified RDE-3 (left) compared with wild type (right). FIG. 7 shows a comparison of the tailing activity of an RDE-3 mutant with an in-frame deletion of residues 113-211 (left) compared with wild type (right). FIG. 8 shows the tailing activity of a G93E-modified RDE-3 (left) and a D189N-modified RDE-3 (right). FIG. 9 shows the tailing activity of an RDE-3 with an in-frame deletion of residues 164-441 (left) and an RDE-3 with an in-frame deletion of residues 169-441 (right). FIG. 10 shows the inactive or low tailing activity of two biological replicates of an RDE-3 with a G366R mutation in the nucleotide recognition motif. FIG. 11 shows a table summarizing the resulting activity from these mutations, showing a lack of activity, as well as the G366R mutation, which showed inactive or low activity. These results confirm the importance of the NTD and PAPd to the poly(UG) polymerase activity of RDE-3.

Example 3. Poly(UG) Polymerase Activity of RDE-3 on Alternative RNA

The method of Example 1 was repeated by substituting an RNase P RNA for the reporter tRNA. The procedure was identical to that described above in Example 1, except that the 5' primer used for PCR contains a sequence specific for the RNase P RNA (5' GTCTGCAGGTCGACTCTAGAAA 3' SEQ ID NO:47). The RNase P RNA reporter contains two MS2 stem loops. FIG. 12A shows the procedure for measuring RDE-3 activity on the RNase P RNA, and FIG. 12B shows representative tail sequences that were observed. These results confirm that RDE-3 exhibits poly(UG) polymerase activity on multiple distinct RNAs.

Example 4. Poly(UG) Polymerase Activity of RDE-3 in an Additional Non-Native Organism 30 ng of mRNA encoding a fusion protein of RDE-3 with MS2 coat protein were injected into a Xenopus laevis oocyte. After six hours, 150 pg of reporter RNA containing three MS2 stem loops were injected into the oocyte. After sixteen hours, total RNA was isolated by lysing the oocytes with a pestle followed by extraction with TRI Reagent® (Sigma-Aldrich, St. Louis, Mo.) as described previously (Kwak and Wickens 2007). The adapter sequence was added to the 3' end of the RNA and reverse transcription was performed as described above. The resulting cDNA was PCR amplified using a 5' primer specific to the reporter RNA (5' CTCTGCAGTCGATAAAGAAAACATGAG 3' SEQ ID NO:48). The PCR products underwent TOPO® cloning according to manufacturer's instructions (available from ThermoFisher Scientific, Waltham, Mass.) and Sanger sequencing. This procedure was repeated twice and is outlined in FIG. 13A. FIG. 13B shows the sequences of tails added to the reporter RNA in each of two experiments. In the first instance, 16 of 43 sequenced reporter RNAs contained UG tails. In the second instance, 11 of 31 sequenced reporter RNAs contained UG tails. These results show that approximately 40% of reporter mRNA was UG-tailed by RDE-3 in X. laevis oocytes. Moreover, these results demonstrate that RDE-3 has poly(UG) polymerase activity in multiple organisms.

Example 5. A Poly(CA)$_8$ DNA Oligomer can Prime Reverse Transcription of a UG-Tailed Reporter tRNA To determine if an added UG tail could allow for reverse transcription primed by a poly(CA) DNA oligomer, a BY4741 yeast strain expressing RDE-3 fused to MS2 coat protein and the reporter tRNA, or a BY4741 yeast strain expressing vector and the reporter tRNA were grown as described in Example 1. RNA was isolated, DNase-treated, and purified, as described in Example 1. The resulting RNA was reverse transcribed with the ImPromII™ reverse transcription system (available from Promega, Madison, Wis.) using a (CA)$_8$ DNA oligomer (5' CACACACACACA-CACA 3' SEQ ID NO:49). The resulting cDNA was PCR amplified using a 5' primer specific to nucleotides 1-24 of tRNA reporter (5' GGCAACTTGGCCGAGTGGTTAAGG 3' SEQ ID NO:50) and a 3' primer specific for the added tail and nucleotides 64-76 of the reporter tRNA (5' CACACA-CACACACACA TGGCGACAACTGC 3' SEQ ID NO:51). As a control for DNA contamination, extracted RNA from the RDE-3 and vector samples that was not reverse transcribed was also PCR amplified. The resulting PCR products were run on an agarose gel, stained with ethidium bromide, and imaged on a UV lightbox. A PCR product was only observed with the RDE-3-containing sample, indicating that UG tailing can allow for reverse transcription with a poly (CA) DNA primer.

Prophetic Example 6. In Vitro Poly(UG) Polymerase Activity of RDE-3

An RNA substrate, such as a total RNA sample, a purified RNA, a radiolabeled RNA, or a labeled RNA, will be in vitro tailed by a poly(UG) polymerase (UG tailing). The predicted reaction conditions are shown in Table 1. The poly(UG) polymerase and RNA substrate amounts are for a 25 µl reaction volume, and can be scaled relative to a desired reaction volume. Alternatively, the reaction conditions disclosed in Wahle (1991), Martin and Keller (1998), Aphasizhev et al. (2002), Read et al. (2002), Rissland et al. (2007), and Kwak and Wickens (2007) can be used.

The components in Table 1 will be mixed together, absent the RNA substrate. Then, the mixture will be added to the RNA substrate and incubated at 20-37° C. for 10 minutes to 24 hours. Reaction conditions (e.g. incubation time, nucleotide concentration, enzyme concentration) can be modified to produce a longer or shorter UG tail on the RNA substrate. Addition of UG repeats to the RNA substrate can be confirmed by running the tailed substrate on a gel appropriate for the molecular weight of the RNA sample (e.g. polyacrylamide or agarose). Successful tailing will increase the molecular weight of the RNA substrate and will appear as a shift upward in the gel or as a smear in the gel corresponding to a higher molecular weight.

TABLE 1

| Reagent | Alternative | Final concentration in poly(UG) polymerase reaction |
| --- | --- | --- |
| Tris-HCl, pH 7 to 8.3 | | 10-70 mM |
| KCl | KH$_2$PO$_4$, KAc | 10-70 mM |
| EDTA | | 0-3 mM |
| DTT | | 0.1-1 mM |
| MgCl$_2$ | MnCl$_2$, CoCl$_2$, ZnCl$_2$ | 0.05-20 mM |
| BSA | | 0-1 µg/µL |
| RNase inhibitor | | 20-50 Units |
| rUTP | dUTP, dTTP, UTP analog (see below) | 0.05-50 mM |
| rGTP | dGTP, GTP analog (see below) | 0.05-50 mM |
| Poly(UG) polymerase | | 10 pg-2 µg |
| RNA substrate | | trace (radiolabeled)-1 mg (total RNA) |

Prophetic Example 7. Cleanup of Poly(UG) Polymerase Reaction Prior to Downstream Use Following addition of poly(UG) tails to RNA, RDE-3 and unincorporated nucleotides will be removed by standard phenol-chloroform extraction followed by ethanol precipitation. Alternatively, one will remove these components and buffer salts by using a column-based RNA purification kit or a standard G25 column. Following cleanup, this RNA will be used for downstream applications. If a certain size or size range of RNA is desired, one will run the UG-tailed RNA on an appropriate type of gel, excise the desired RNAs, elute the desired RNAs from the gel, and proceed with downstream applications.

Prophetic Example 8. Utilizing Poly(UG) Tails to Amplify Substrate RNAs with Poly(CA) DNA Primer Added UG tails enable two approaches to amplify RNAs with an unknown 3' end sequence (see Prophetic Example 9 for the second). First, because the UG tail has a known sequence of alternating uridine and guanine residues, one will use a poly(CA) DNA oligomer as a primer for reverse transcription of cDNA. The reaction mixture shown in Table 2 will be utilized to reverse transcribe the UG-tailed RNAs using a DNA oligomer to prime cDNA synthesis. It may be necessary to remove unincorporated nucleotides, perform buffer exchange, or remove the poly(UG) polymerase enzyme prior to reverse transcription. This can be achieved by performing a cleanup step as described in Prophetic Example 7.

Following reverse transcription, one will amplify the DNA products in one of two ways, depending on the type of RNA substrate. First, if the sequence of the RNA of interest is known, one will use a DNA primer complementary to the sequence of the RNA as the 5' primer and poly(CA) as the 3' primer for PCR amplification. Alternatively, if the sequence of the RNA is not known, or if there is a mixture of RNAs in the starting sample, one will use a random hexamer or decamer DNA oligomer as the 5' primer and poly(CA) as the 3' primer for PCR amplification.

As a control for specificity of the poly(CA) primer for the UG tail, one should also perform the identical reverse transcription and PCR procedures with RNA that is not UG-tailed. Due to the specificity of the poly(CA) primer for the UG tail, only the UG-tailed RNA should result in a robust product, in comparison to the control, following the above procedure. We anticipate that longer poly(CA) primers will be more specific for longer UG tails, based on the higher melting temperature of the resulting duplexes. PCR products should be analyzed on an appropriate gel to verify the expected molecular weight(s).

TABLE 2

| Reagent | Amount needed for a 20 µL reaction |
| --- | --- |
| UG-tailed RNA | 20 ng-2 µg |
| poly(CA) DNA primer (8-20 CA repeats) | 0.5-50 pmol |
| reverse transcriptase (RT) of choice | Follow manufacturer's guidelines |
| appropriate RT buffer with MgCl$_2$ | Follow manufacturer's guidelines |

Prophetic Example 9. Utilizing Poly(UG) Tails to Reverse Transcribe Substrate RNAs with Poly(UG) Intramolecular Primer Prior to PCR Amplification Second, UG tails of sufficient length can form a secondary structure that "folds back" on itself and can serve as an intramolecular RNA primer for reverse transcriptase activity. It has previously been established that reverse transcriptases can use an RNA primer for DNA synthesis in vitro (Myers et al. 1980; Kohlstaedt and Steitz 1992), so the UG tail will be used as an intramolecular primer for reverse transcription of cDNA. It may be necessary to remove unincorporated nucleotides, perform buffer exchange, or remove the poly(UG) polymerase enzyme prior to reverse transcription. This can be achieved by performing a cleanup step as described in Prophetic Example 7.

One should verify that the UG tail is more than 8 nucleotides; we anticipate that longer UG tails will promote more efficient and specific intramolecular pairing of the UG tail. To achieve such intramolecular pairing, the UG-tailed RNA should be incubated in the presence of salts (e.g. MgCl$_2$ or NaCl) at concentrations appropriate for secondary structure formation. The UG-tailed RNA in the salt-containing buffer will be heated to reduce secondary structure and then slowly cooled to allow for annealing of the UG tail to itself.

Following this annealing step, the reaction mixture shown in Table 3 will be utilized to reverse transcribe the UG-tailed RNAs in the absence of a DNA oligomer to prime cDNA synthesis by using the UG tail as an intramolecular primer. Annealing and reverse transcription should also be performed with RNA that is not UG-tailed to confirm that the RNA sample alone does not allow for reverse transcription in the absence of a DNA primer.

Following reverse transcription, one will amplify the cDNA products in one of two ways, depending on the type of RNA substrate. First, if the sequence of the RNA of interest is known, one will use a DNA primer complementary to the sequence of the RNA as the 5' primer and poly(CA) as the 3' primer for PCR amplification. Alternatively, if the sequence of the RNA is not known, or if there is a mixture of RNAs in the starting sample, one will use a random hexamer or decamer DNA oligomer as the 5' primer and poly(CA) as the 3' primer for PCR amplification.

TABLE 3

| Reagent | Amount needed for a 20 µL reaction |
| --- | --- |
| UG-tailed RNA | 20 ng-2 µg |
| reverse transcriptase (RT) of choice | Use up to 3-fold additional enzyme, as compared to manufacturer's guidelines |
| appropriate RT buffer with MgCl$_2$ | Follow manufacturer's guidelines |

Prophetic Example 10. Alternative Nucleotides for Poly(UG) Polymerase Activity

UTP or GTP may be substituted with nucleotide analogs or with deoxynucleotides (dUTP, dGTP, dTTP). It is important to note that GTP, UTP, or both can be substituted with the corresponding nucleotide analog, or a nucleotide analog can be added along with GTP or UTP to partially label the UG tail. Addition of a UG tail containing nucleotide analogs or with deoxynucleotides can be visualized by running a portion of the reaction products on a gel, and visualizing the RNA by staining and/or direct visualization (e.g. via fluorescent nucleotides). It might be necessary to remove unmodified RNA prior to performing downstream applications.

The type of nucleotide analog to choose will be indicated by the intended downstream application. For example, labeled rUTP, including 4-Thio-UTP, biotin-labeled UTP, digoxigenin-11-UTP, fluorescently-labeled UTP (e.g. UTP-Cy3, UTP-Cy5), can be substituted in order to visualize and/or purify the RNA using the labeled UG tail. An advantage of RDE-3 poly(UG) polymerase activity for addition of biotinylated nucleotide tails is that RDE-3 adds alternating U and G nucleotides, and thus has the potential to add alternating biotinylated and unmodified nucleotides. To accomplish this, one will substitute one unmodified nucleotide (U or G) for a biotinylated nucleotide analog and proceed with the UG tailing reaction. This alternating pattern of addition may alleviate RNA aggregates that have been observed previously (Moritz and Wahle 2014) with addition of many biotinylated nucleotides to the 3' end of the RNA.

An alternative chemical approach to synthesize a labeled UG tail is to use nucleotide analogs with the appropriate reactive groups for click chemistry (e.g. Azido-C3-UTP, 5-Ethynyl-UTP), as has been demonstrated by Winz and colleagues (Winz et al. 2012).

In addition, the poly(UG) polymerase reaction will be used to add deoxynucleotides to the 3' end of RNA, as has been shown for yeast poly(A) polymerase (Lingner & Keller 1993).

Obviously, many modifications and variations of the present invention are possible in light of the above teachings and may be practiced otherwise than as specifically described while within the scope of the appended claims.

SEQUENCE LISTING STATEMENT

The application includes the sequence listing that is concurrently filed in computer readable form. This sequence listing is incorporated by reference herein.

REFERENCES

Aphasizhev, R., et al. (2002). Trypanosome Mitochondrial 3' Terminal Uridylyl Transferase (TUTase): The Key Enzyme in U-Insertion/Deletion RNA Editing. *Cell,* 108, 637-648.

Coller, J. and Wickens, M. (2007). Tethered Function Assays: An Adaptable Approach to Study RNA Regulatory Proteins. *Method Enzymol,* 429, 299-321.

Kohlstaedt, L. A. and Steitz, T. A., (1992). Reverse transcriptase of human immunodeficiency virus can use either human tRNA$_3^{Lys}$ or *Escherichia coli* tRNA$_2^{Gln}$ as a primer in an in vitro primer-utilization assay. *Proc Natl Acad Sci USA,* 89, 9652-9656.

Kwak, J. E., and Wickens, M. (2007). A family of poly(U) polymerases. RNA 13, 860-867.

Lingner, J. and Keller, W. (1993). 3'-end labeling of RNA with recombinant yeast poly(A) polymerase. *Nucleic Acids Res,* 21(12), 2917-2920.

Martin, G. and Keller, W. (1998). Tailing and 3'-end labeling of RNA with yeast poly(A) polymerase and various nucleotides. *RNA,* 4, 226-230.

Moritz, B. and Wahle, E. (2014). Simple methods for the 3' biotinylation of RNA. RNA, 20, 421-427.

Myers, J. C., Dobkin, C., and Spiegelman, S. (1980). *Proc Natl Acad Sci USA,* 77(3), 1316-1320.

Read, R. L., et al. (2002). Cytoplasmic poly(A) polymerases mediate cellular responses to S phase arrest. *Proc Natl Acad Sci USA,* 99, 12079-12084.

Rissland, O. S., Mikulasova, A., and Norbury, C. J. (2007). Efficient RNA Polyuridylation by Noncanonical Poly(A) Polymerases. *Mol Cell Biol,* 27(10), 3612-3624.

Wahle, E. (1991). Purification and Characterization of a Mammalian Polyadenylate Polymerase Involved in the 3' End Processing of Messenger RNA Precursors. *J Biol Chem,* 266(5), 3131-3139.

Winz, M., et al. (2012). Site-specific terminal and internal labeling of RNA by poly(A) polymerase tailing and copper-catalyzed or copper-free strain-promoted click chemistry. *Nucleic Acids Res,* 40(10), e78.

We claim:

1. A method for adding a poly(UG) sequence to an end of an RNA substrate, the method comprising:
   (a) expressing a poly(UG) polymerase from a construct comprising a poly(UG) polymerase activity sequence linked to a heterologous promoter;
   (b) contacting the RNA substrate with the poly(UG) polymerase; and
   (c) allowing the poly(UG) polymerase to add a poly(UG) sequence to the end of the RNA substrate by retaining contact between the RNA substrate and the poly(UG) polymerase for a period of time from about 1 second to about 28 days.

2. The method of claim 1, wherein the poly(UG) polymerase is C. elegans RDE-3.

3. The method of claim 1, wherein the poly(UG) polymerase comprises at least a portion of NCBI Reference Sequence NP_491834.1.

4. The method of claim 1, wherein the method is performed in vitro.

5. The method of claim 1, wherein the method additionally comprises
   (d) priming cDNA synthesis with a poly(CA) primer.

6. The method of claim 1, wherein the period of time of step (c) is a first length of time and is sufficient to introduce a poly(UG) tail having a length sufficient to form a hairpin between a 5' portion of the poly(UG) tail with a 3' portion of the poly(UG) tail, and wherein the method additionally comprises;
   (d) waiting a second length of time sufficient to allow formation of the hairpin; and
   (e) priming cDNA or cRNA synthesis with the poly(UG) tail as a primer.

7. The method of claim 5, wherein the poly(UG) polymerase is *C. elegans* RDE-3.

8. The method of claim 6, wherein the poly(UG) polymerase is *C. elegans* RDE-3.

9. The method of claim 1, wherein the sequence of the RNA substrate is unknown.

10. The method of claim 1, wherein the poly(UG) polymerase is a fusion protein comprising a poly(UG) polymerase activity domain and an RNA-interaction domain.

11. The method of claim 10, wherein the poly(UG) polymerase activity domain includes at least a portion of *C. elegans* RDE-3.

12. The method of claim 10, wherein the RNA-interaction domain is MS2 coat protein or another RNA-binding protein.

* * * * *

UNITED STATES PATENT AND TRADEMARK OFFICE
CERTIFICATE OF CORRECTION

PATENT NO. : 10,301,605 B2  
APPLICATION NO. : 14/943229  
DATED : May 28, 2019  
INVENTOR(S) : Marvin P. Wickens and Melanie A. Preston Page 1 of 1

It is certified that error appears in the above-identified patent and that said Letters Patent is hereby corrected as shown below:

In the Specification

Column 6, Line 29 "$x_{7-43}$" should read --$x_{7-13}$--.

Column 8, Line 27 "TURBOT"" should read --TURBO™--.

Signed and Sealed this  
Twentieth Day of August, 2019

Andrei Iancu  
*Director of the United States Patent and Trademark Office*